United States Patent
Kim et al.

(10) Patent No.: US 9,968,317 B2
(45) Date of Patent: May 15, 2018

(54) RADIATION IMAGING APPARATUS

(71) Applicant: SAMSUNG ELECTRONICS CO., LTD., Suwon-si (KR)

(72) Inventors: Jawoon Kim, Seoul (KR); Eun-hye Seo, Bucheon-si (KR); Pil-yong Oh, Gwangmyeong-si (KR); Soon-tae Lee, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 215 days.

(21) Appl. No.: 15/131,609

(22) Filed: Apr. 18, 2016

(65) Prior Publication Data

US 2016/0345922 A1    Dec. 1, 2016

(30) Foreign Application Priority Data

May 27, 2015    (KR) .................. 10-2015-0073922

(51) Int. Cl.
*A61B 6/00*    (2006.01)
*A61B 6/03*    (2006.01)

(52) U.S. Cl.
CPC ............ *A61B 6/4429* (2013.01); *A61B 6/032* (2013.01); *A61B 6/035* (2013.01); *A61B 6/587* (2013.01); *A61B 6/461* (2013.01); *A61B 6/467* (2013.01)

(58) Field of Classification Search
CPC ................................ A61B 6/4429; H05G 1/02
See application file for complete search history.

(56) References Cited

U.S. PATENT DOCUMENTS

| | | |
|---|---|---|
| 5,054,041 A | 10/1991 | Hampel |
| 5,469,429 A | 11/1995 | Yamazaki et al. |
| 5,672,010 A | 9/1997 | MacNicol et al. |
| 6,447,164 B1 | 9/2002 | Polkus |
| 6,592,312 B1 | 7/2003 | Tutikawa |
| 6,917,665 B2 | 7/2005 | Nakanishi et al. |
| 7,654,739 B2 | 2/2010 | Lumma et al. |
| 8,681,930 B2 | 3/2014 | Sharpless et al. |
| 2003/0035506 A1* | 2/2003 | Tybinkowski ......... A61B 6/035 378/4 |

FOREIGN PATENT DOCUMENTS

| | | |
|---|---|---|
| CN | 101953715 A | 1/2011 |
| JP | 3-173540 A | 7/1991 |
| KR | 2001-0023513 A | 3/2001 |

OTHER PUBLICATIONS

International Search Report (PCT/ISA/210) and Written Opinion (PCT/ISA/237) dated Jul. 25, 2016 issued by the International Searching Authority in counterpart International Application No. PCT/KR2016/003755.

* cited by examiner

*Primary Examiner* — Dani Fox
(74) *Attorney, Agent, or Firm* — Sughrue Mion, PLLC

(57) ABSTRACT

A radiation imaging apparatus includes: a housing configured to be hollow and extend along a first axial direction; a radiation emitter configured to be disposed in the housing and emit radiation along an optical axial direction perpendicular to the first axial direction; protruding units configured to extend along a second axial direction perpendicular to the first axial direction and the optical axial direction, and disposed to be fixed to both sides of the radiation emitter; and pressing units including an inclined unit disposed to contact at least one of the protruding units, so that the inclined unit and the at least one of the protruding units support each other.

19 Claims, 20 Drawing Sheets

RADIATION IMAGING APPARATUS

CROSS-REFERENCE TO RELATED APPLICATION

This application claims priority from Korean Patent Application No. 10-2015-0073922, filed on May 27, 2015, in the Korean Intellectual Property Office, the disclosure of which is incorporated herein in its entirety by reference.

BACKGROUND

1. Field

The present disclosure relates to methods and apparatuses for radiation imaging.

2. Description of the Related Art

A radiation imaging apparatus may include various imaging modes such as an X-ray apparatus, a computerized tomography (CT) apparatus, an ultrasonic apparatus, an electron beam CT apparatus, a magnetic resonance imaging (MRI) apparatus, or the like.

The radiation imaging apparatus includes a radiation source and a radiation detector which are disposed to face each other. Radiation emitted from the radiation source passes through a patient, and reaches the radiation detector. The radiation detector may generate an image by detecting variable attenuation of the received radiation.

However, if a subject is exposed to radiation for a long period of time, tissues of the subject may be damaged, and various diseases may be caused. A subject, a radiation emitter, and a radiation detector need to be precisely aligned so as to prevent such side effects. For example, an adjustment apparatus that may adjust a location of a radiation emitter may be used for a medical radiation apparatus. The subject, the radiation emitter, and the radiation detector may be aligned by manually or automatically controlling a location adjustor included in the radiation imaging apparatus.

SUMMARY

Provided are radiation imaging apparatuses that may adjust an alignment state of a radiation emission apparatus and a radiation detection apparatus and methods of operating the same.

Additional aspects will be set forth in part in the description which follows and, in part, will be apparent from the description, or may be learned by practice of the presented exemplary embodiments.

According to an aspect of an exemplary embodiment, a radiation imaging apparatus includes: a housing configured to be hollow and extend along a first axial direction; a radiation emitter configured to be disposed in the housing and emit radiation along an optical axial direction perpendicular to the first axial direction; a plurality of protruding units configured to extend along a second axial direction perpendicular to the first axial direction and the optical axial direction of the radiation, and disposed to be fixed to both sides of the radiation emitter; and a plurality of pressing units including an inclined unit disposed to contact a protruding unit so that the inclined unit and the protruding unit support each other.

The inclined unit may form a first angle with the optical axial direction of the radiation, and a first protruding unit and a second protruding unit may be disposed to face each other at both sides of the radiation emitter, and the radiation emitter may move along the second axial direction as a first pressing unit and a second pressing unit, which are disposed so that the first pressing unit and the first protruding unit support each other and the second pressing unit and the second protruding unit support each other, move in directions different from each other along the optical axial direction of the radiation.

The radiation imaging apparatus may further include a plurality of first lead screws that are respectively disposed to be inserted into the plurality of pressing units, and move the plurality of pressing units along the optical axial direction of the radiation as the plurality of first lead screws rotate.

The radiation imaging apparatus may further include a plurality of first bearings configured to be disposed at an end of each of the plurality of first lead screws and support the plurality of first lead screws so that the plurality of first lead screws may rotate.

A degree to which the radiation emitter moves according to rotation of the plurality of first lead screws may be determined by a number of times the plurality of first lead screws rotate and the first angle with respect to the inclined unit.

The radiation imaging apparatus may further include: a support unit disposed to be fixed to the radiation emitter; and one or more second lead screws disposed to be inserted into the support unit, and the support unit is moved along the first optical axial direction as one or more second lead screws rotate.

The radiation imaging apparatus may further include: a second bearing configured to be disposed at an end of the second lead screw and support the second lead screw so that the plurality of second lead screws may rotate.

A degree to which the radiation emitter moves along the first axial direction may be determined according to a number of times the second lead screw rotates.

The inclined unit mat form a second angle with the first axial direction, and a first protruding unit and a second protruding unit may be disposed to face each other at both sides of the radiation emitter, and the radiation emitter may move along the second axial direction as a first pressing unit and a second pressing unit, which are disposed so that the first pressing unit and the first protruding unit support each other and the second pressing unit and the second protruding unit support each other, move in directions different from each other along the first axial direction.

The radiation imaging apparatus may further include a plurality of first lead screws disposed to be inserted into the plurality of pressing units, and the plurality of pressing units may be moved along the first axial direction as the plurality of first lead screws rotate.

The radiation imaging apparatus may further include a plurality of first bearings that are disposed at an end of each of the plurality of first lead screws and support the plurality of first lead screws so that the plurality of first lead screws may rotate.

A degree to which the radiation emitter moves according to rotation of the plurality of first lead screws may be determined according to a number of times the plurality of first lead screws rotate and the second angle with respect to the inclined unit.

According to an aspect of another exemplary embodiment, a radiation imaging apparatus includes: a housing configured to be hollow and extend along a first axial direction; a radiation emitter configured to be disposed in the housing and emit radiation along an optical axial direction perpendicular to the first axial direction; a plurality of protruding units that are formed to extend along a second axial direction perpendicular to the first axial direction and the optical axial direction of the radiation, and disposed to be fixed to both sides of the radiation emitter; and a plurality of pressing units each including a side surface having a shape of a cone, which has a generating line formed to establish a third angle with the optical axial direction of the radiation, and disposed so that the side surface contacts each of the plurality of protruding units, and thus, the side surface and the protruding unit support each other.

A first protruding unit and a second protruding unit, and a third protruding unit and a fourth protruding unit may be respectively disposed to face each other at both ends of the radiation emitter, and the radiation emitter may be tilted with respect to the optical axial direction of the radiation, as a first pressing unit and a second pressing unit, which are disposed so that the first pressing unit and the first protruding unit support each other and the second pressing unit and the second protruding unit support each other, move along the optical axial direction of the radiation in different directions from each other and a third pressing unit and a fourth pressing unit, which are disposed so that the third pressing unit and the third protruding unit support each other and the fourth pressing unit and the fourth protruding unit support each other, are fixed to the third pressing unit and the fourth protruding unit.

The radiation emitter may move along the second axial direction as the first pressing unit and the third pressing unit, and the second pressing unit and the fourth pressing unit respectively may move in directions opposite to each other along the first axial direction of the radiation.

The radiation imaging apparatus may further include a plurality of first lead screws disposed to be inserted into the plurality of pressing units, and the plurality of pressing units may be moved along the optical axial direction of the radiation as the plurality of first lead screws rotate.

The radiation imaging apparatus may further include a plurality of first bearings that are disposed at an end of each of the plurality of first lead screws and support the plurality of first lead screws so that the plurality of first lead screws may rotate.

A degree to which the radiation emitter moves according to rotation of the plurality of first lead screws may be determined by a number of times the plurality of first lead screws rotate and the third angle between the generating line and the side surface.

The radiation imaging apparatus may further include a support unit disposed to be fixed to the radiation emitter; and one or more second lead screws disposed to be inserted into the support unit, and the support unit is moved along the first optical axial direction as one or more second lead screws rotate.

The radiation imaging apparatus may further include a second bearing configured to be disposed at the second lead screw and support the second lead screw so that the second lead screw may rotate.

A degree to which the radiation emitter moves along the first axial direction may be determined according to a number of times the plurality of second lead screws rotate.

According to an aspect of another exemplary embodiment, a radiation imaging apparatus includes: a housing configured to be hollow and extend along a first axial direction; a radiation emitter configured to be disposed in the housing and emit radiation along an optical axial direction perpendicular to the first axial direction; and a bracket that is disposed between the radiation emitter and the housing and supports the radiation emitter so that the radiation emitter is fixed to the housing, wherein one surface of the bracket, which is disposed to face one surface of the housing extending in an optical axial direction of the radiation, and the surface of the housing are tilted in correspondence with a fourth angle in the optical axial direction of the radiation.

The radiation imaging apparatus may further include one or more bolt units that are formed to extend in the first axial direction, and disposed so that an end of each of the one or more bolt units are fixed to the surface of the housing; and one or more through holes disposed at the bracket to respectively correspond to the one or more bolt units.

The fourth angle may be equal to or less than 5.6°.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
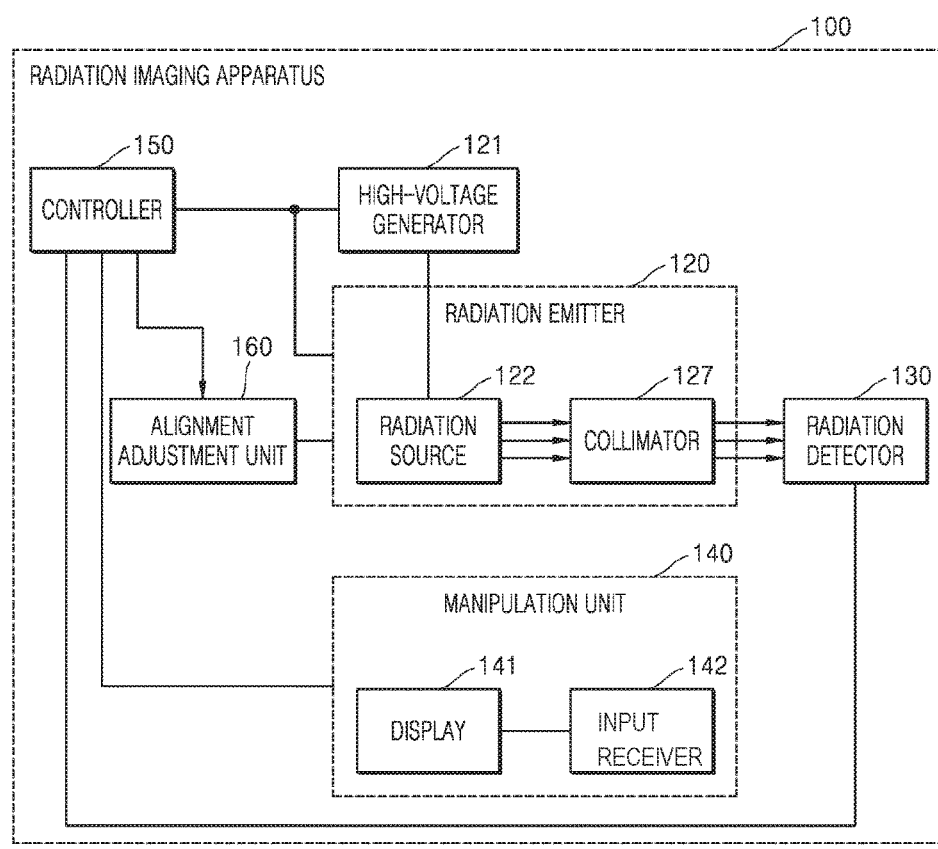
FIG. 1 illustrates a block diagram of a radiation imaging apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list. Embodiments are provided so that this disclosure will be thorough and complete, and will fully convey the concept of the exemplary embodiments to those of ordinary skill in the art, and the scope of embodiments should be defined by the appended claims.

Terms used herein will be briefly described, and the exemplary embodiments will be described in detail below.

General and widely-used terms have been employed herein, in consideration of functions provided in the exemplary embodiments, and may vary according to an intention of one of ordinary skill in the art, a precedent, or emergence of new technologies. Additionally, in some cases, an applicant may arbitrarily select specific terms. Then, the applicant will provide the meaning of the terms in the description of the exemplary embodiments. Accordingly, It will be understood that the terms, used herein, should be interpreted as having a meaning that is consistent with their meaning in the context of the relevant art and will not be interpreted in an idealized or overly formal sense unless expressly so defined herein.

An "image", described herein, may refer to multi-dimensional data consisting of discrete image elements (for example, pixels in a two-dimensional (2D) image or voxels in a three-dimensional (3D) image). An example of an image may include a medical image of a subject which is obtained from an X-ray apparatus, a CT (computerized tomography) apparatus, a magnetic resonance imaging (MRI) apparatus, an ultrasonic apparatus, or other medical imaging apparatuses.

A "subject", described herein, may refer to a person, an animal, or a part of a person or an animal. For example, the subject may include at least one selected from the group consisting of an organ such as a liver, a heart, a womb, a brain, breast, or abdomen, and a blood vessel. Additionally, the "subject" may be a phantom. A phantom refers to a material whose density, effective atomic number, and volume are very close to those of a living thing. A phantom may include a spherical phantom having a property similar to that of a human body.

A "user", described herein, refers to a medical professional such as a doctor, a nurse, a medical laboratory technologist, a medical image specialist, or an engineer who repairs a medical apparatus, but is not limited thereto.

A radiation imaging apparatus is a medical imaging apparatus for obtaining an image of an internal structure of a human body by transmitting a radiation beam into a human body. The radiation imaging apparatus may obtain a medical image of a subject easily in a short period of time compared to other medical imaging apparatuses such as an MRI apparatus or a CT apparatus. Accordingly, the radiation imaging apparatus is widely used for plain chest radiography, plain abdominal radiography, plain skeletal radiography, plain sinus radiography, plain neck soft tissue radiography, breast radiography, or the like.

Figure 2A:
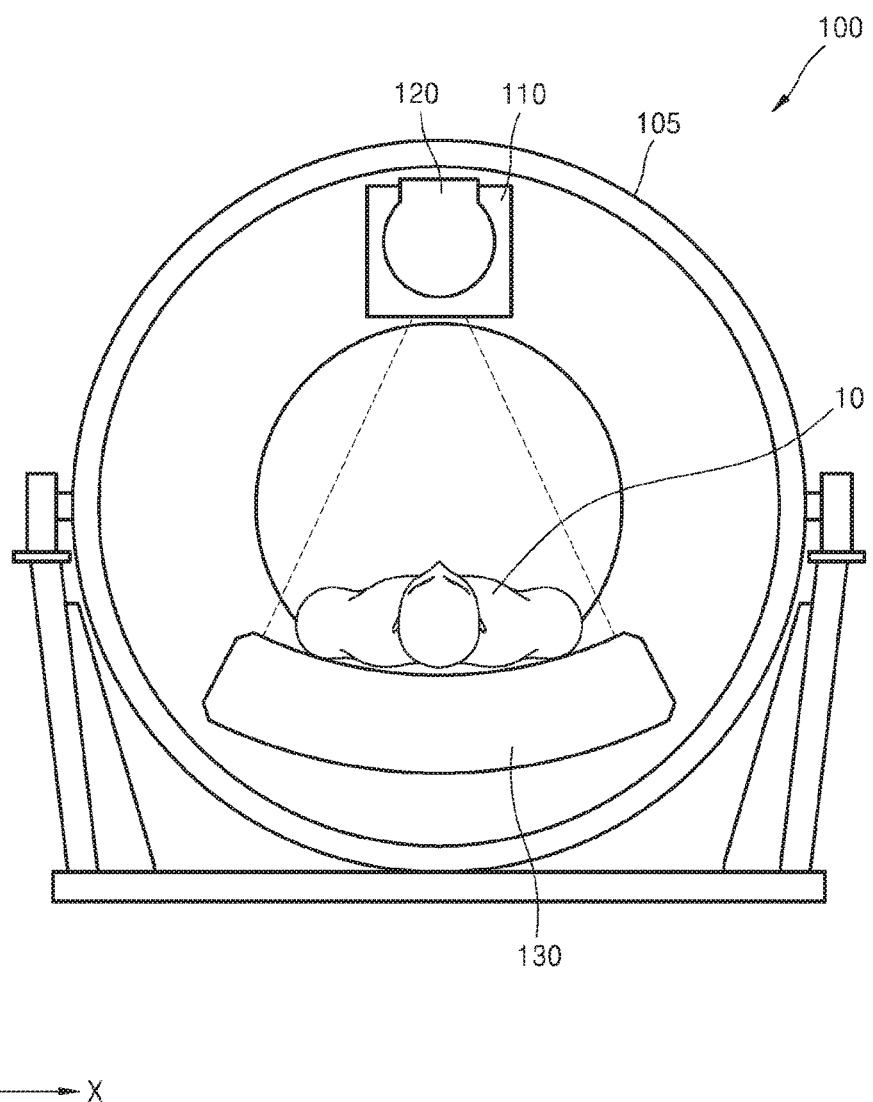
FIG. 2A illustrates a front view of the radiation imaging apparatus according to an exemplary embodiment.
Figure 2B:
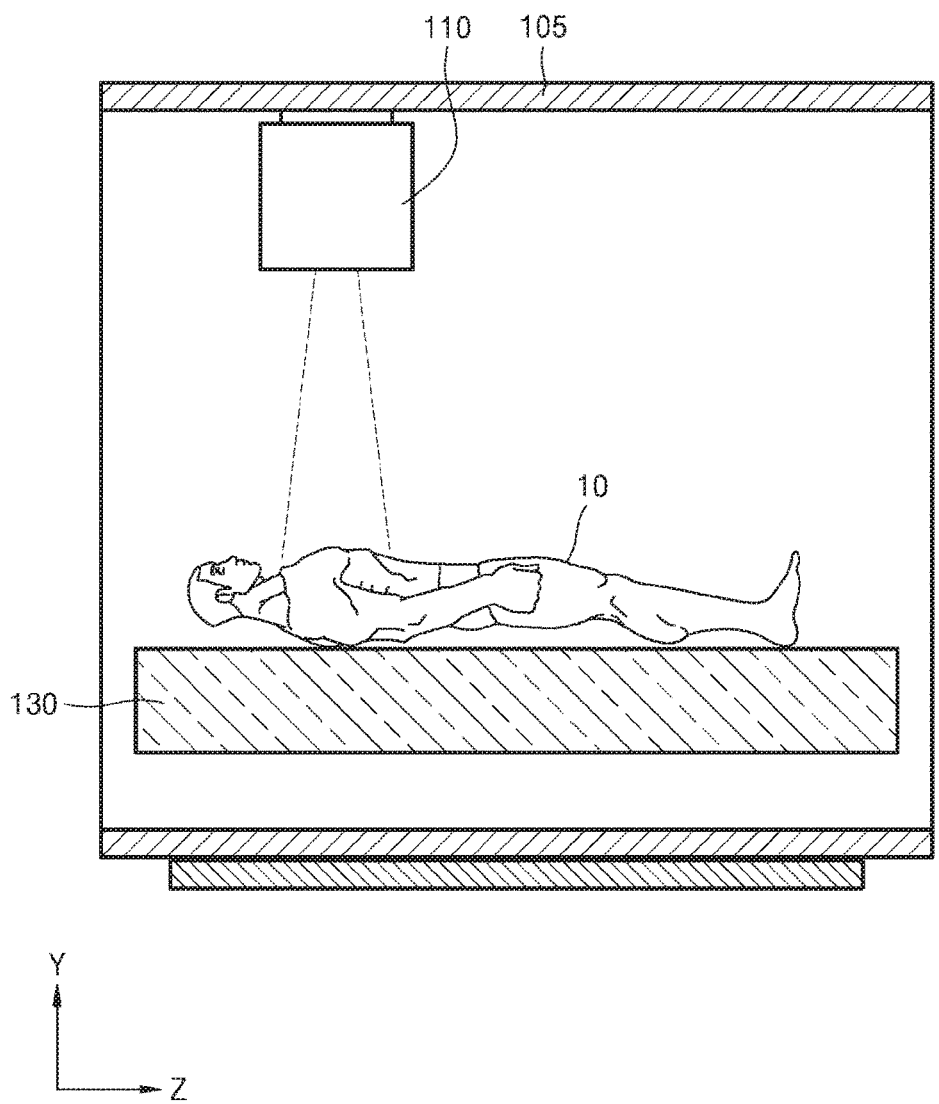
FIG. 2B illustrates a side-sectional view of the radiation imaging apparatus shown in FIG. 2A.

FIG. 1 illustrates a block diagram of a radiation imaging apparatus 100 according to an exemplary embodiment, FIG. 2 illustrates a front view of the radiation imaging apparatus 100 according to an exemplary embodiment, and FIG. 2B illustrates a side-sectional view of the radiation imaging apparatus 100 shown in FIG. 2A.

Referring to FIGS. 1, 2A, and 2B, the radiation imaging apparatus 100 may include a housing 105, a radiation emitter 120, a high-voltage generator 121, a radiation detector 130, a manipulation unit 150, a controller 150, and an alignment adjustment unit 160. The controller 150 may control all operations of the radiation imaging apparatus 100. The radiation imaging apparatus 100 may be a mobile apparatus, or a fixed apparatus as shown in FIGS. 2A and 2B.

The housing 105 is an apparatus that may accommodate the radiation emitter 120 or a subject 10. As an example, the housing 105 may be formed to be hollow and extend in a direction in which the subject 10 enters the housing 105, as shown in FIGS. 2A and 2B. The radiation emitter 120 may be disposed inside the housing 105.

The high-voltage generator 121 generates a high voltage for generating radiation and applies the high voltage to a radiation source 122.

The radiation emitter 120 may include the radiation source 122 for receiving the high voltage generated from the high-voltage generator 121 and generates and emits radiation, and a collimator 127 for adjusting an area, toward which radiation is emitted, by guiding a path of the radiation emitted from the radiation source 122.

For example, if the radiation imaging apparatus 100 is an X-ray apparatus that may emit an X-ray, the radiation source 122 may include an X-ray tube, and the X-ray tube may be formed of a two-pole vacuum tube having a cathode and an anode. The radiation source 122 creates a high-vacuum state of about 10 mmHg inside the X-ray tube, heats a filament of a cathode to a high temperature, and thus, generates thermal electrons. For example, a tungsten filament may be used as the filament of the cathode, and the filament of the cathode may be heated by applying a voltage of 10 V and a current of 3 to 5 A to an electrical conductive wire connected to the filament. If a high voltage of 10 to 300 kVp is applied between the cathode and the anode, thermal electrons are accelerated and collide with target materials in the cathode and the anode, and thus, an X-ray may be generated. The generated X-ray is emitted toward the outside through an optical window. The optical window may be formed by using barium film. If a high voltage is applied between the cathode and the anode, most of energy of the thermal electrons that collide with the target material is consumed as heat, and remaining energy other than the consumed energy is converted into an X-ray.

A voltage applied between the cathode and the anode is referred to as a tube voltage. The tube voltage is applied by the high-voltage generator 121, and a magnitude of the tube voltage may be expressed as a peak value in kVp. If a tube voltage is increased, a speed of a thermal electron is increased and, as a result, energy (energy of a photon) of an X-ray generated when the thermal electron collides with a target material is increased. A current flowing through the X-ray tube is referred to as a tube current, and may be expressed as an average value of currents flowing through the X-ray tube in mA. If a tube voltage is increased, a number of thermal electrons emitted from a filament is increased and, resultantly, an X-ray dose (a number of X-ray photons) generated when the thermal electrons collide with a target material is increased. Accordingly, energy of the X-ray may be controlled by the tube voltage, and a strength of the X-ray or an X-ray dose may be controlled by the tube current and X-ray exposure time.

The radiation detector 130 may detect radiation that was emitted from the radiation emitter 120 and has passed through a subject. The radiation detector 130 may be a digital detector. The radiation detector 130 may include a light-receiving surface (not shown) on which an X-ray emitted from the radiation source 122 may be incident. The light-receiving surface may be implemented by using a thin-film transistor (TFT) or a charge coupled device (CCD). The radiation detector 130 may be formed as a mobile apparatus that may move to a certain location or rotate, or a fixed apparatus that is fixed at a predetermined location as shown in FIGS. 2A and 2B.

The manipulation unit 140 may include an display 141 and an input receiver 142. The input receiver 142 may receive from a user an input of a command for manipulating the radiation imaging apparatus 100 and various information regarding radiography. The controller 150 may control or manipulate the radiation imaging apparatus 100 based on information input to the input receiver 142. The display 141 may output information related to radiography such as information about radiation emission under control of the controller 150.

An example of the input receiver 142 may be a keyboard, a mouse, a touchscreen, a voice recognizer, a fingerprint reader, an iris recognizer, or an input apparatus that is obvious to one of ordinary skill in the art. A user may input a command for emitting radiation via the input receiver 153. The input receiver 142 may include a switch for inputting such a command.

The controller 150 controls locations of the radiation emitter 120 and the radiation detector 130, radiographing timing, and a radiographing condition, according to a radiographing condition set by the user.

In detail, the controller 150 may control a timing at which radiation is emitted, a strength of the radiation, an area toward which the radiation is emitted by controlling the radiation source 122 and the radiation detector 130 according to a command input via the input receiver 142. Additionally, the control unit 150 may adjust a location of the radiation detector 130 according to a certain radiographing condition, and control a timing at which the radiation detector 130 is operated. Additionally, the controller 150 may generate a medical image of the subject 10 by using image data received via the radiation detector 130. In detail, the controller 150 may receive image data from the radiation detector 130, remove noise from the image data, and then, adjust a dynamic range and perform interleaving, thus generating a medical image of the subject 10.

The display 141 may output a medical image generated by the controller 150. The display 141 may output information that is necessary for a user to manipulate the radiation imaging apparatus 100, such as a user interface (UI), user information, or subject information. An example of the display 141 may be a speaker, a printer, a cathode ray tube (CRT) display, a liquid-crystal display (LCD), a plasma display panel (PDP), an organic light-emitting display (OLED), a field emission display (FED), a light-emitting display (LED), a variable frequency drive (VFD) display, a digital light processing (DLP) display, a flat panel display (FPD), a three-dimensional (3D) display, a transparent display, or other various output apparatuses that are obvious to one of ordinary skill in the art.

The alignment adjustment unit 160 is an adjustment member for adjusting alignment of the radiation emitter 120, the subject 10, and the radiation detector 130 by moving the radiation emitter 120 or the radiation detector 130. If the radiation emitter 120, the subject 10, and the radiation detector 130 are detected as being misaligned, the alignment adjustment unit 160 may automatically move the radiation emitter 120 or the radiation detector 130 by using a driving motor (not shown) and the controller 150, and manually move the radiation emitter 120 or the radiation detector 130 so as to adjust a fine alignment error. Hereinafter, the alignment adjustment unit 160 that may adjust alignment of the subject 10, the radiation emitter 120, and the radiation detector 130 by using a manual method is described. For convenience of description, as shown in FIGS. 2A and 2B, a first axial direction in which the subject 10 enters the radiation imaging apparatus 100 is determined as a direction parallel to a Z-axis, an optical axial direction in which radiation is emitted from the radiation emitter 120 is determined as a direction parallel to a Y-axis, and a direction perpendicular to the Z-axis and the Y-axis is determined as a direction parallel to an X-axis.

Figure 3A:
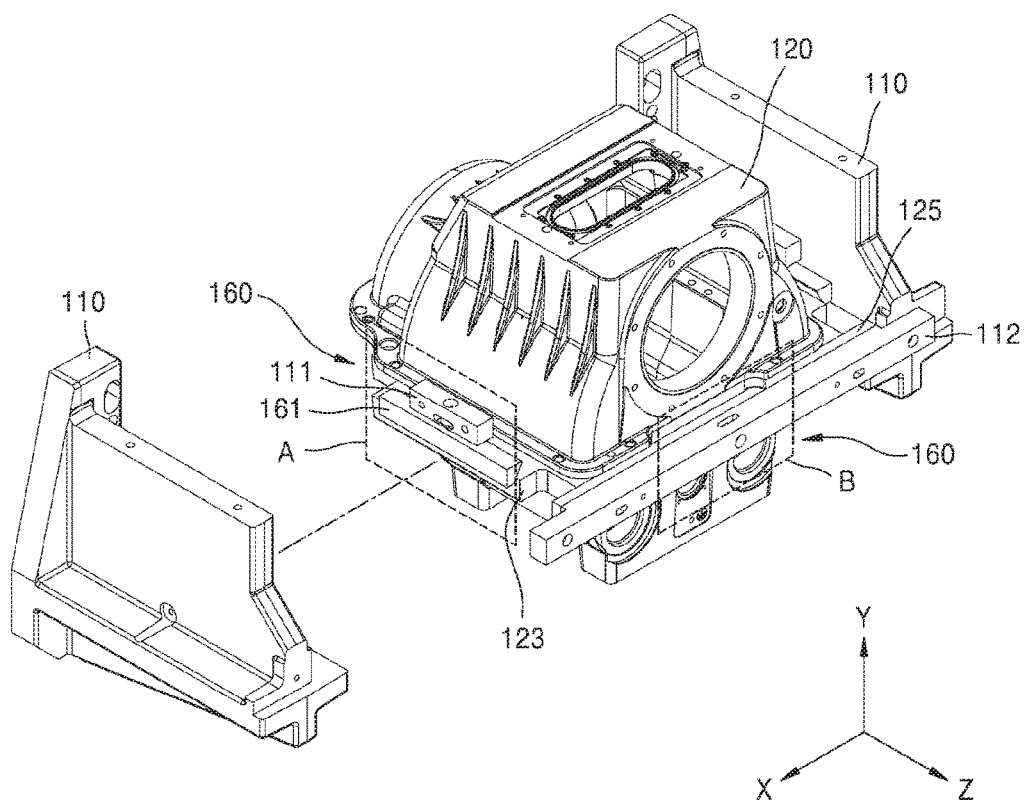
FIG. 3A illustrates a schematic perspective view of an example of a radiation emitter and an alignment adjustment unit.
Figure 3B:
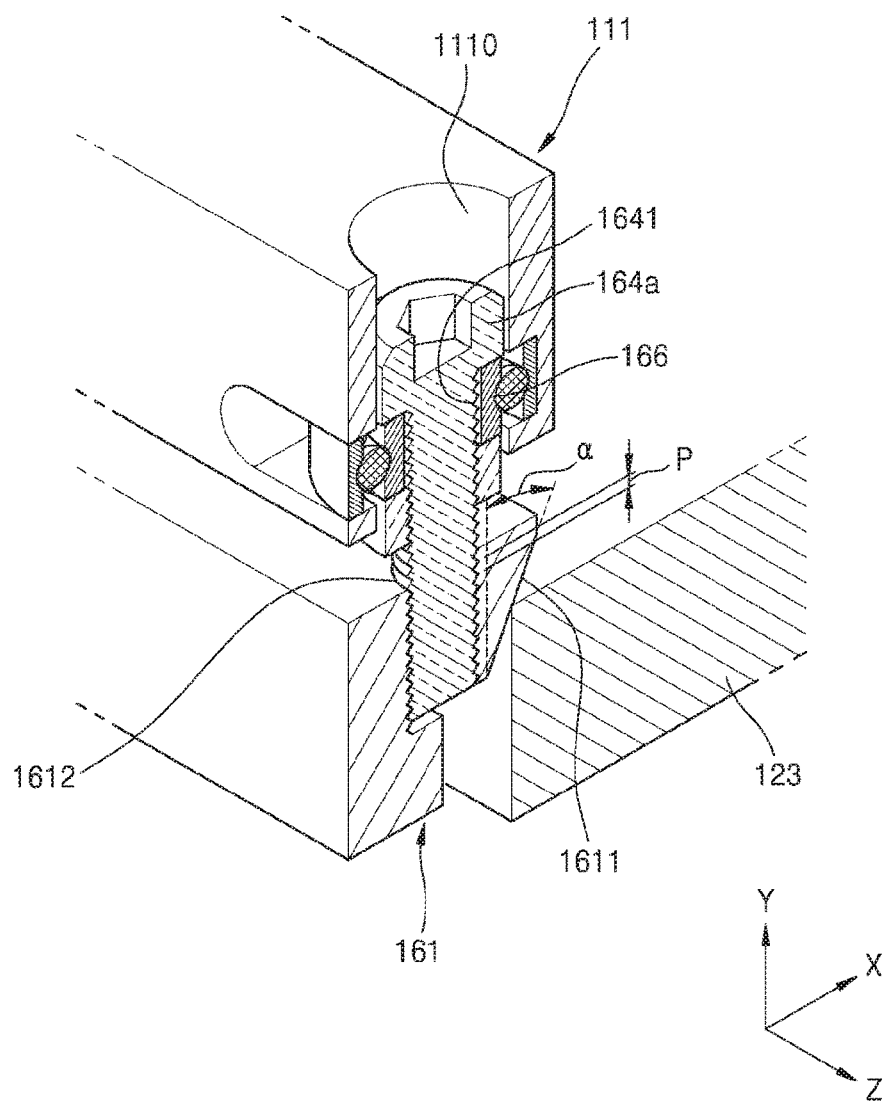
FIG. 3B illustrates a magnified perspective view of an area A shown in FIG. 3A.
Figure 3C:
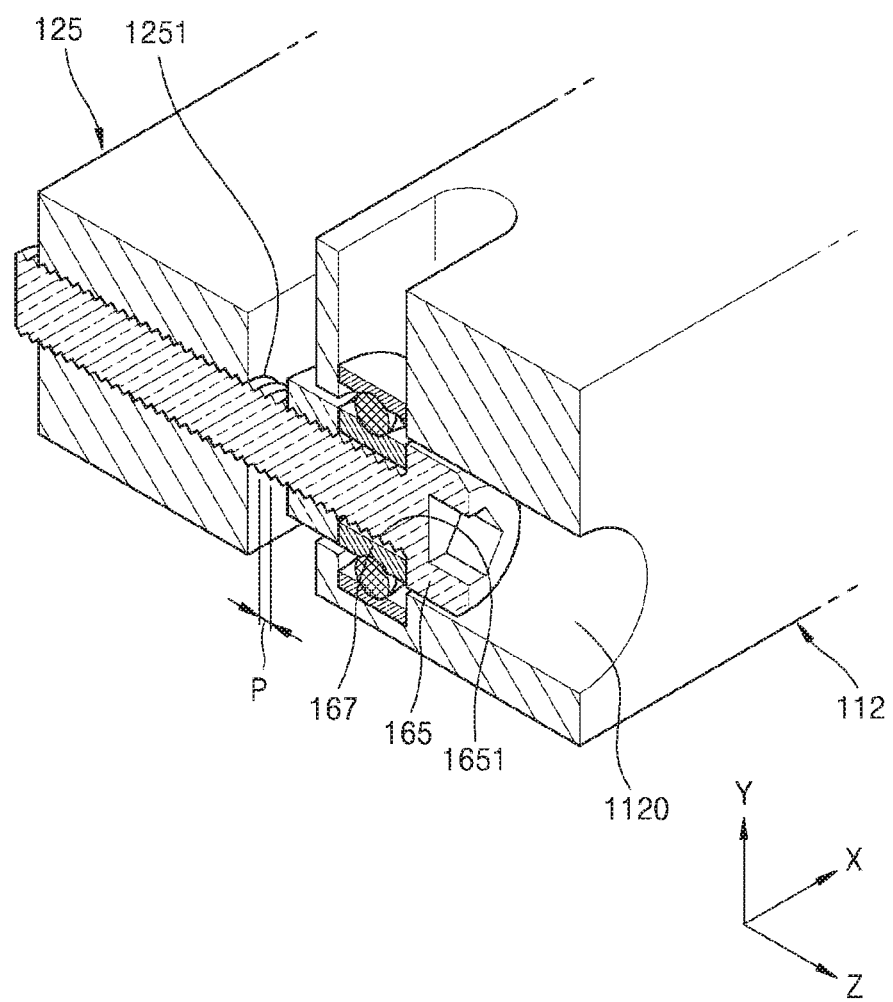
FIG. 3C illustrates a magnified perspective view of an area B shown in FIG. 3A.

FIG. 3A illustrates a schematic perspective view of an example of the radiation emitter 120 and the alignment adjustment unit 160 which are shown in FIG. 2, FIG. 3B illustrates a magnified perspective view of an area A shown in FIG. 3A, and FIG. 3C illustrates a magnified perspective view of an area B shown in FIG. 3A.

Referring to FIGS. 3A through 3C, according to an exemplary embodiment, the radiation emitter 120 may be disposed to be supported by the housing 105 by using a support body 110 that is disposed to be fixed to the housing 105. The alignment adjustment unit 160 may adjust alignment of the subject 10, the radiation emitter 120, and the radiation detector 130 by moving a location of the radiation emitter 120 with respect to the support body 110.

The alignment adjustment unit 160 may include a first pressing unit 161 and a second pressing unit 162 that may respectively press and move a first protruding unit 123 and a second protruding unit 124 which are fixed to both sides of the radiation emitter 120, a support unit 125 that is fixed to the radiation emitter 120 and may move the radiation emitter 120 in a Z-axis direction, first lead screws 164a and 164b that may move the first and second pressing units 161 and 162, a second lead screw 165 that may move the support unit 125, and first and second bearings 166 and 167 respectively disposed at sides of the first lead screws 164a and 164b and the second lead screw 165.

The first protruding unit 123 and the second protruding unit 124 are driving force-delivering members that are disposed to be fixed to both sides of the radiation emitter 120 and may deliver a force, applied from outside, to the radiation emitter 120. As an example, the first protruding unit 123 and the second protruding unit 124 may deliver a force, applied from outside, to the radiation emitter 120, and thus, move the radiation emitter 120 in an X-axis direction. The first protruding unit 123 and the second protruding unit 124 may respectively contact and be supported by the first pressing unit 161 and the second pressing unit 162 which will be described later, and the first protruding unit 123 and the first pressing unit 161, and the second protruding unit 124 and the second pressing unit 162 may be respectively disposed to face each other at both ends of the radiation emitter 120.

The first pressing unit 161 and the second pressing unit 162 are pressing members that may respectively apply a force to the first protruding unit 123 and the second protruding unit 124 in a second axial direction. The first pressing unit 161 and the second pressing unit 162 may respectively include first and second inclined units 1611 and 1621 that may contact the first protruding unit 123 and the second protruding unit 124, and first insertion holes 1612 and 1622 into which the first lead screws 164a and 164b may be inserted.

The first inclined unit 1611 may be formed to be inclined at a first angle α with respect to a Y-axis, in a clockwise direction. The second inclined unit 1621 may be formed to be inclined at the first angle α with respect to the Y-axis, in a counterclockwise direction. For example, the first and second inclined units may have linear inclined surfaces facing one another, or may have conical surfaces a normal of which forms a first angle with respect to the optical axial direction. Accordingly, if the first pressing unit 161 and the second pressing unit 162 move along the Y-axis respectively in different directions from each other, the first protruding unit 123 and the second protruding unit 124 that contact and are supported by the first and second inclined units 1611 and 1621 may receive a force from the first and second pressing units 161 and 162 in an X-axis direction.

Threads, with which screws formed on the first lead screws 164a and 164b are engaged and rotate, may be formed on an inner wall of the first insertion holes 1612 and 1622.

The support unit 125 is a driving force-delivering member that is disposed to be fixed to a front surface of the radiation emitter 120, and may move the radiation emitter 120 in a Z-axis direction by delivering a force, applied from outside, to the radiation emitter 120. The support unit 125 may include a second insertion hole 1251 into which the second lead screw 165, which is to be described later, may be inserted. Threads, with which screws formed on the second lead screw 165 may be engaged and rotate, may be formed on an inner wall of the second insertion hole 1251.

The first and second lead screws 164a, 164b, and 165 may be formed in the shape of a rod extending in a direction of one side, and screw threads 1641 and 1651 may be formed on at least a part of the first and second lead screws 164a, 164b, and 165. Threads of the first and second lead screws 164a, 164b, and 165 may be disposed at certain intervals. The first lead screws 164a and 164b may be inserted into the first insertion holes 1612 and 1622, and may move the first pressing unit 161 and the second pressing unit 162 in the Y-axis direction. The second lead screw 165 may be inserted into the second insertion hole 1651 and move the support unit 125 in the Z-axis direction.

First and second fixed units 111 and 112 are support members that are disposed to be fixed to the support body 110 and may support the alignment adjustment unit 160. The first and second fixed units 111 and 112 may include first and second adjustment holes into which the first and second lead screws 164a, 164b, and 165 may be inserted. A user may adjust a location of the radiation emitter unit 120 by inserting an adjustment tool into the first and second adjustment holes 1110 and 1120 and rotating the first and second lead screws 164a, 164b, and 165.

The first and second bearings 166 and 167 are disposed at an end of the first and second lead screws 164a, 164b, and 165 in a direction of lengths of the first and second lead screws 164a, 164b, and 165. The first and second bearings 166 and 167 rotatably support the first and second lead screws 164a, 164b, and 165. A lubricant (not shown) may be disposed between the first and second bearings 166 and 167 and the first and second screws 164a, 164b, and 165 so that the first and second lead screws 164a, 164b, and 165 may smoothly rotate around the first and second bearings 166 and 167. The first and second bearings 166 and 167 may be supported by the first and second fixed units 111 and 112 which are fixed to the housing 105 and, as described above, rotatably support the first and second lead screws 164a, 164b, and 165.

Figure 4A:
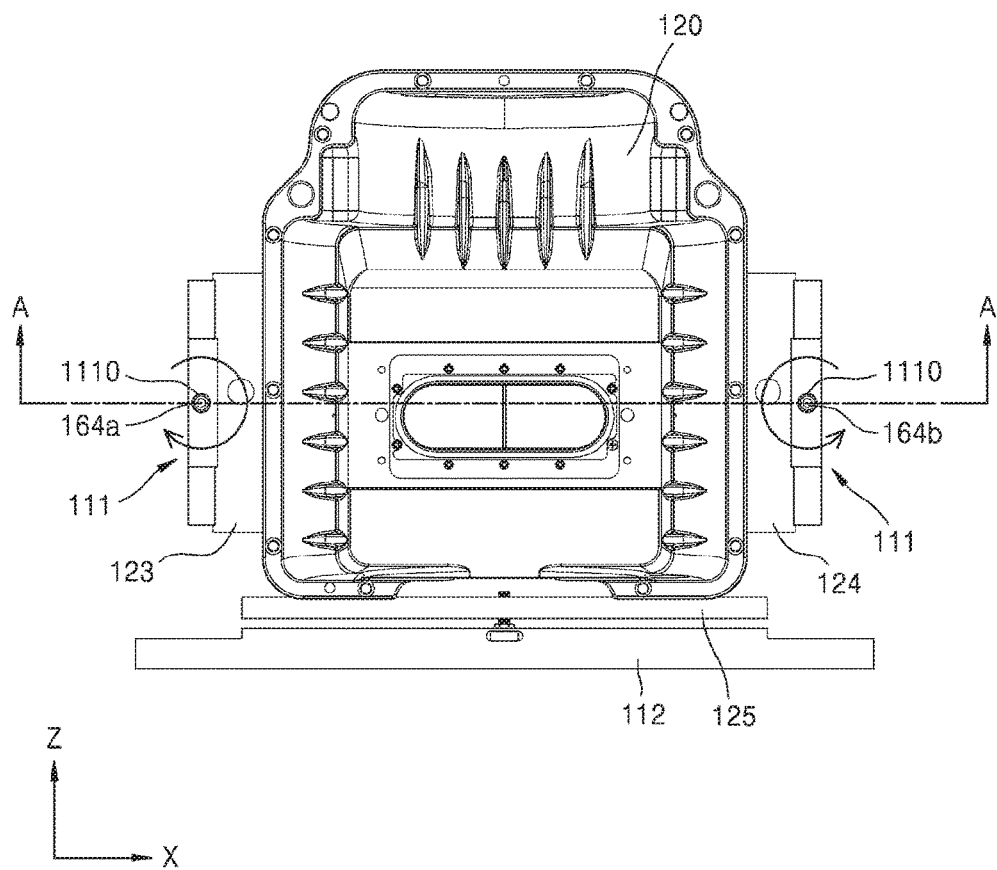
FIG. 4A illustrates a plan view of the radiation emitter, shown in FIG. 3A, for explaining movement of a location in an X-axis direction.
Figure 4B:
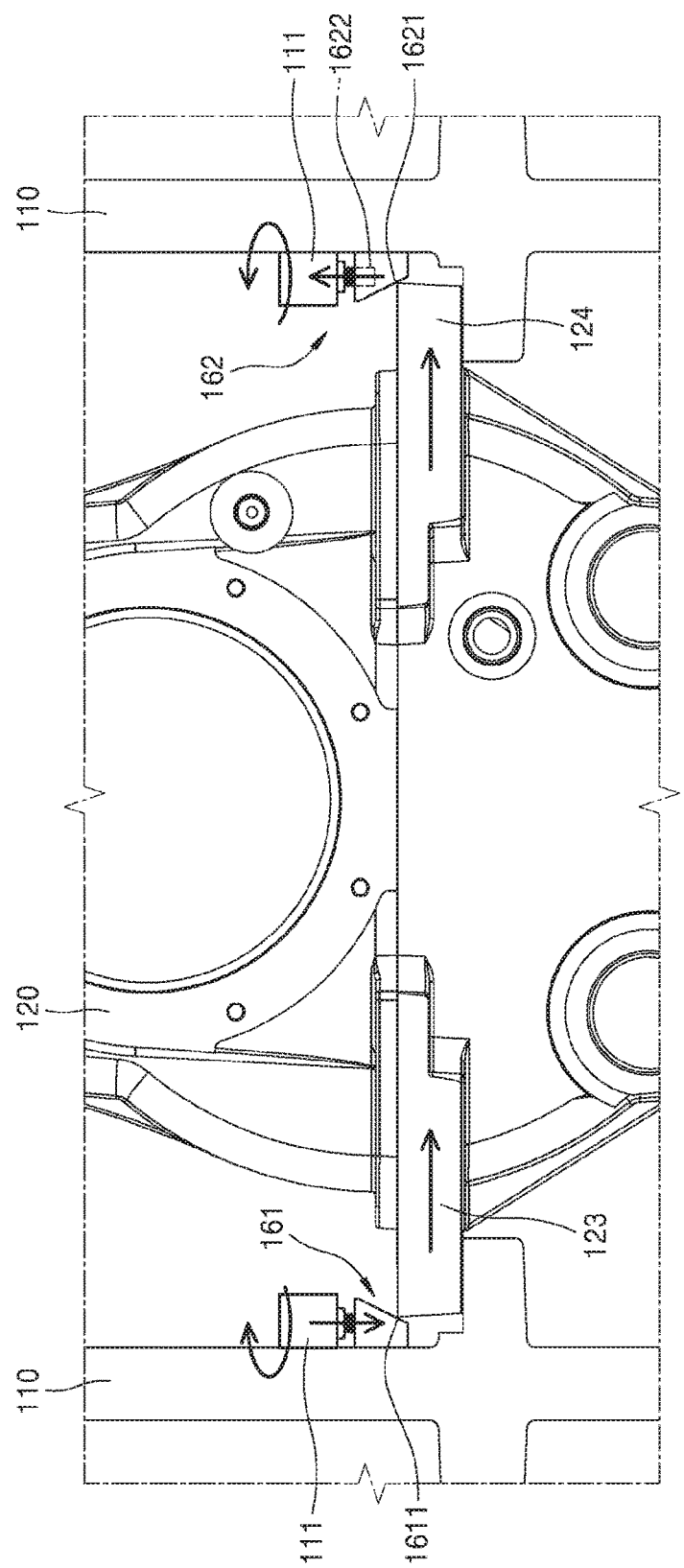
FIG. 4B illustrates a sectional view of the radiation emitter, shown in FIG. 4A, which is taken along a line A-A.

FIG. 4A illustrates a plan view of the radiation emitter 120, shown in FIG. 3A, for explaining movement of a location in an X-axis direction, and FIG. 4B illustrates a sectional view of the radiation emitter 120, shown in FIG. 4A, which is taken along line A-A.

Referring to FIGS. 3B, 4A, and 4B, if a user inserts a precision adjustment tool (not shown) into the first adjustment hole 1110 and rotates the first lead screw 164a in a clockwise direction, the first lead screw 164a may be moved in a direction in which radiation is emitted along the Y-axis direction. As an example, the first adjustment hole 1110 may be disposed at a side of the radiation emitter 120 and, accordingly, the user may easily insert the precision adjustment tool into the first adjustment hole 1110 along a direction in which the first adjustment hole 1110 disposed at the side of the radiation emitter 120 extends.

As an example, as described above, as the first lead screws 164a and 164b rotates in a clockwise direction, the screw threads 1641 of the first lead screw 164a may rotate to be engaged with a screw thread formed on an inner wall of the first insertion hole 1612. Accordingly, the first lead screw 164a may move the first pressing unit 161 in a direction in which radiation is emitted in the Y-axis direction. The first bearing 166 may support the first lead screw 164a to rotate around the first fixed unit 111.

If the user rotates the first lead screw 164a by inserting the precision adjustment tool (not shown) into the first adjustment hole 1110 and, at the same time, rotates the first lead screw 164b in a counterclockwise direction by inserting the precision adjustment tool into the first adjustment hole 1110, the first lead screw 164b may be moved in a direction opposite to a direction in which the first lead screw 164a moves. As an example, if the first lead screw 1674b rotates in a counterclockwise direction, the screw threads 1641 of the first lead screw 164b may rotate to be engaged with a screw threads formed on an inner wall of the first insertion hole 1612. Accordingly, the first lead screw 164b may move the second pressing unit 162 in a direction in which the first lead screw 164a is moved. The first bearing 166 may support the second lead screw 164b so that the second lead screw 164b may rotate around the first fixed unit 111.

As the first pressing unit 161 and the second pressing unit 162 move along the Y-axis in different directions from each other, one of the first protruding unit 123 and the second protruding unit 124 may receive a force along the X-axis direction from contacted one of the first pressing unit 161 and the second pressing unit 162, and the other of the first protruding unit 123 and the second protruding unit 124 may be disengaged from the other of the first pressing unit 161 and the second pressing unit 162. Accordingly, the first protruding unit 123, the second protruding unit 124, and the radiation emitter 120 that is disposed to be fixed to the first protruding unit 123 and the second protruding unit 124 may be moved along the X-axis direction.

A degree in which the radiation emitter 120 moves in the X-axis direction may be determined according to a number of times the first lead screws 164a and 164b rotate and a first angle α with respect to the first inclined unit 1611. As an example, when the screw threads 1641 and 1651 formed on the first lead screws 164a and 164b is moved in correspondence with one pitch P as the first lead screws 164a and 164b rotate once, and the first angle α of the first inclined unit 1611 is 45°, if the first lead screws 164a and 164b rotate once, the radiation emitter 120 may be moved in correspondence with one pitch P of the screw threads 1641 and 1651 formed on the first lead screws 164a and 164b in the X-axis direction. If the first lead screws 164a and 164b rotate twice, the radiation emitter 120 may be moved in correspondence with two pitches P of the screw threads 1641 and 1651 formed on the first lead screws 164a and 164b in the X-axis direction. In other words, since a distance for which the radiation emitter 120 is moved when the first lead screws 164a and 164b rotate once may be determined according to a number of pitches P of the screw threads 1641 of the first lead screws 164a and 164b, which is obtained when the first lead screws 164a and 164b rotate once, and a tangent value for the first angle α, a user may determine an amount of movement of the radiation emitter 120 in the X-axis direction according to a number of times the first lead screws 164a and 164b rotate.

Figure 5:
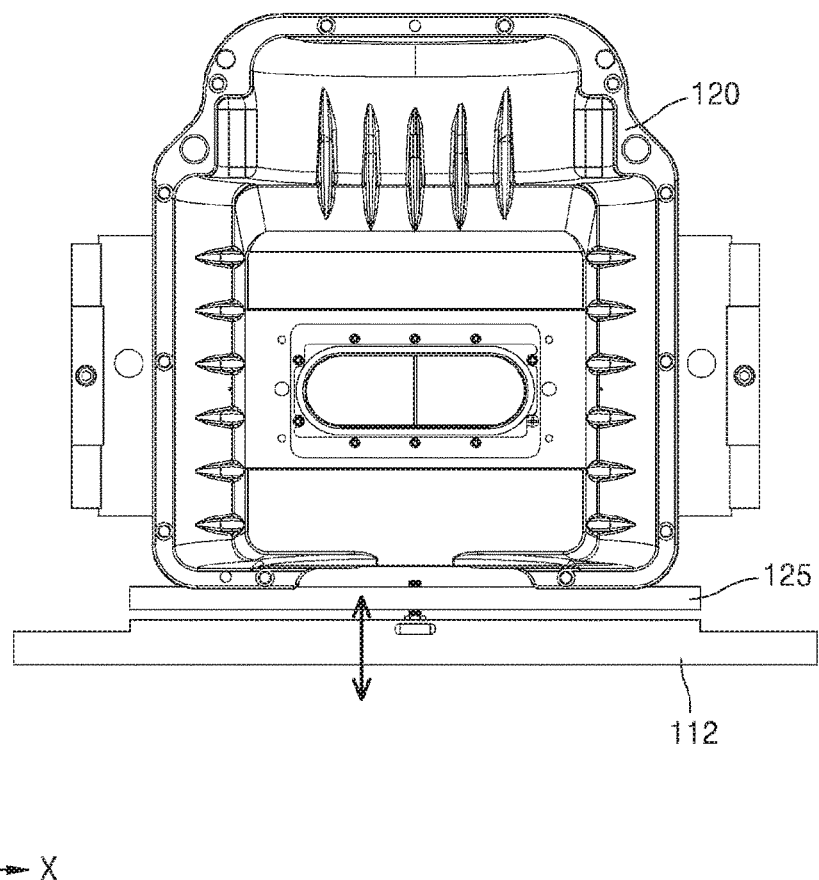
FIG. 5 illustrates a plan view of the radiation emitter, shown in FIG. 3A, for explaining movement of a location in a Z-axis direction.

FIG. 5 illustrates a plan view of the radiation emitter 120, shown in FIG. 3A, for explaining movement of a location in a Z-axis direction.

Referring to FIGS. 3C and 5, if a user inserts the precision adjustment tool into the second adjustment hole 1120 and rotates the second lead screw 165 in a clockwise direction, the second lead screw 165 may be moved in the Z-axis direction. As an example, the second adjustment hole 1120 may be disposed at a front surface of the radiation emitter 120 and, accordingly, a user may easily insert the precision adjustment tool into the second adjustment hole 1120 along a direction in which the second adjustment hole 1120 disposed at the front surface of the radiation emitter 120 extends.

As an example, as described above, if the second lead screw 165 rotates in a clockwise direction, the screw threads 1651 of the second lead screw 165 may rotate to be engaged with a screw formed on an inner wall of the second insertion hole 1251. Accordingly, the second lead screw 165 may move the support unit 125 in a direction in which the subject 10 enters the radiation imaging apparatus 100 along the Z-axis direction. Additionally, if the second lead screw 165 rotates in a counterclockwise direction, the second lead screw 165 may move the support unit 125 in a direction different from the direction in which the subject 10 enters the radiation imaging apparatus 100. The second bearing 167 may support the second lead screw 165 so that the second screw 165 may rotate around the second fixed unit 112.

A degree in which the radiation emitter 120 moves in the Z-axis direction may be determined according to a number of times the second lead screw 165 rotates. As an example, if the screw threads 1651 formed on the second lead screw 165 is moved in correspondence with one pitch P as the second lead screw 165 rotates once, the radiation emitter 120 may be moved in correspondence with one pitch P of the screw threads 1651 formed on the second lead screw 165 along the Z-axis direction when the second lead screw 165 rotates once, and the radiation emitter 120 may be moved in correspondence with two pitches P of the screw threads 1651 formed on the second lead screw 165 along the Z-axis direction when the second lead screw 165 rotates twice. In other words, a distance for which the radiation emitter 120 is moved in the Z-axis direction when the second lead screw 165 rotates once may be determined according to a number of times the second lead screw 165 rotates and a number of pitches P of the screw threads 1651 when the second lead screw 165 rotates once.

As described above, alignment of the radiation emitter 120, the subject 10, and the radiation detector 130 in the X-axis direction and the Z-axis direction may be adjusted by using the first lead screws 164a and 164b and the second lead screw 165. Accordingly, since a user may adjust a location of the radiation emitter 120 by inserting an adjustment tool into the first and second adjustment holes 1110 and 1120 formed on the first and second fixed units 111 and 112 and rotating the first and second lead screws 164a, 164b, and 165, the user may easily adjust alignment of the radiation emitter 120, the subject 10, and the radiation detector 130.

Figure 6A:
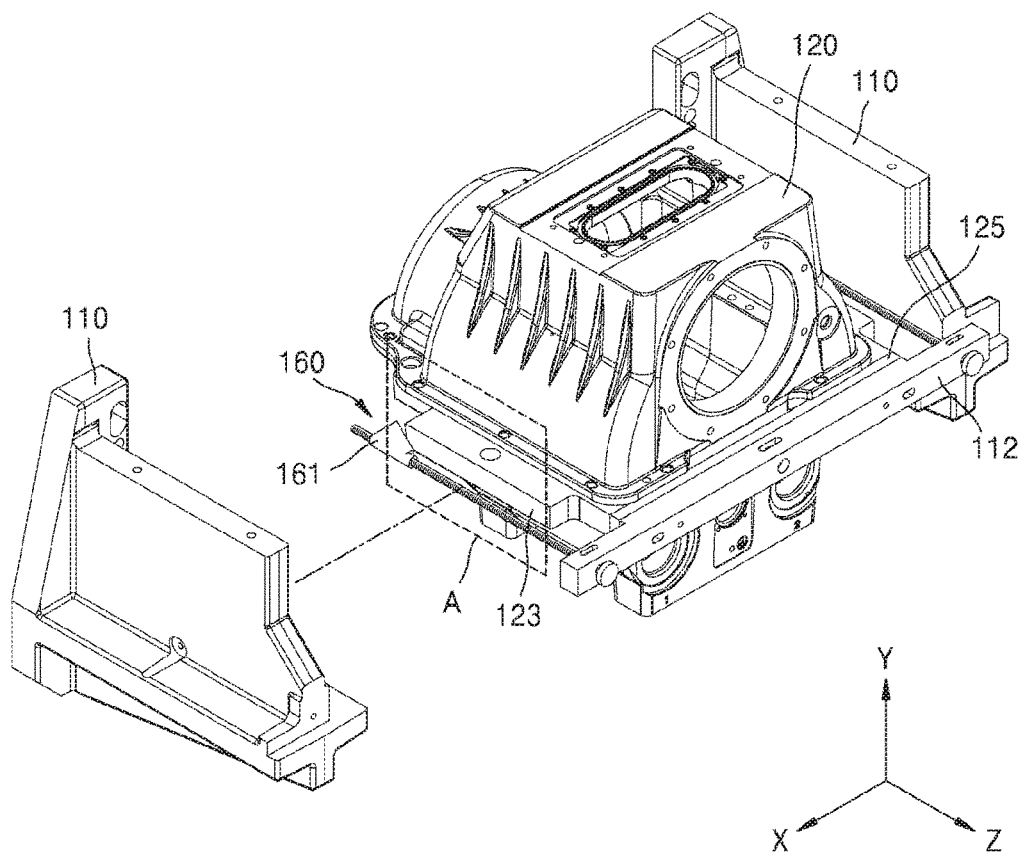
FIG. 6A illustrates a perspective view of the radiation emitter according to another exemplary embodiment.
Figure 6B:
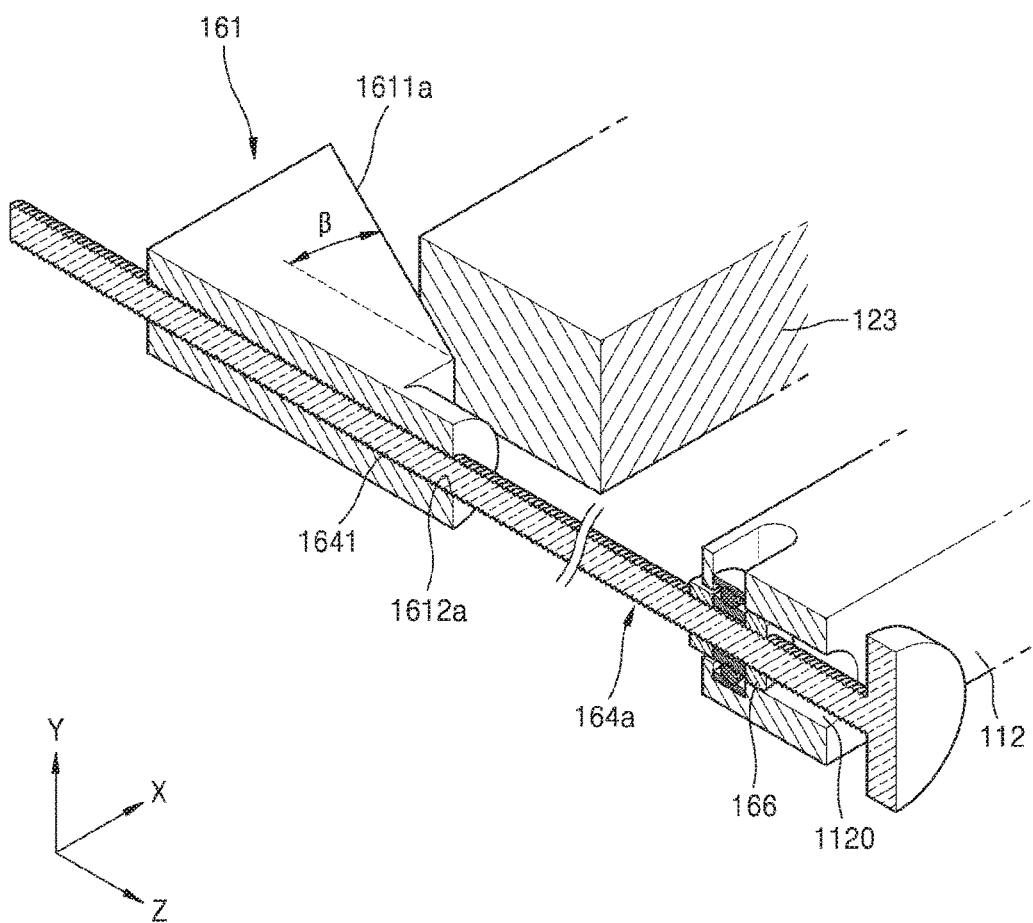
FIG. 6B illustrates a magnified perspective view of an area A shown in FIG. 6A.

FIG. 6A illustrates a perspective view of the radiation emitter 120 according to another exemplary embodiment, and FIG. 6B illustrates a magnified perspective view of an area A shown in FIG. 6A. For convenience of description, a description about elements identical to those shown in FIGS. 3A and 3B is not provided here again.

In the above-described embodiment, a user may adjust alignment of the radiation emitter 120, the subject 10, and the radiation detector 130 in an X-axis direction, by inserting the precision adjustment tool into the first adjustment hole 1110 formed on the first fixed unit 111 and moving the first lead screws 164a and 164b in a Y-axis direction.

On the contrary, shapes of the first pressing unit 161 and the second pressing unit 162 may be changed so as to adjust alignment of the radiation emitter 120, the subject 10, and the radiation detector 130 in the X-axis direction by inserting the first lead screws 164a and 164b in the Z-axis direction.

Referring to FIGS. 6A and 6B, according to another exemplary embodiment, the first pressing unit 161 and the second pressing unit 162 may include first and second inclined units 1611a and 1612a that may contact the first protruding unit 123 and the second protruding unit 124 so as to apply a force to the first protruding unit 123 and the second protruding unit 124 in the X-axis direction, and first insertion holes 1612a and 1622a into which the first lead screws 164a and 164b that may move the first pressing unit 161 and the second pressing unit 162 in the Z-axis direction may be inserted.

The first inclined unit 1611a may be formed to be inclined at a second angle β with respect to a Z-axis, in a clockwise direction. The second inclined unit 1621a may be formed to be inclined at the second angle β with respect to the Z-axis, in a counterclockwise direction. Accordingly, if the first pressing unit 161 and the second pressing unit 162 move along the Z axis respectively in different directions from each other, the first protruding unit 123 and the second protruding unit 124 that contact the first and second inclined units 1611a and 1621a may be moved in a same direction along an X axis. A screw that may be engaged with the screw threads 1641 formed on the first lead screws 164a and 164b and rotate may be formed on an inner wall of the first insertion holes 1612a and 1622a.

The first lead screws 164a and 164b may be formed in the shape of a rod extending toward one side, and disposed in the Z-axis direction. The first adjustment hole 1110 formed on the second fixed unit 112 may be disposed to extend in the Z-axis direction so that the first lead screws 164a and 164b may be inserted into the first adjustment hole 1110 in the Z-axis direction. The first bearing 166 may be disposed at an end of the first lead screws 164a and 164b in a direction of a length of the first lead screws 164a and 164b, and support the first lead screws 164a and 164b so that the first lead screws 164a and 164b may rotate around the second fixed unit 112.

Figure 7:
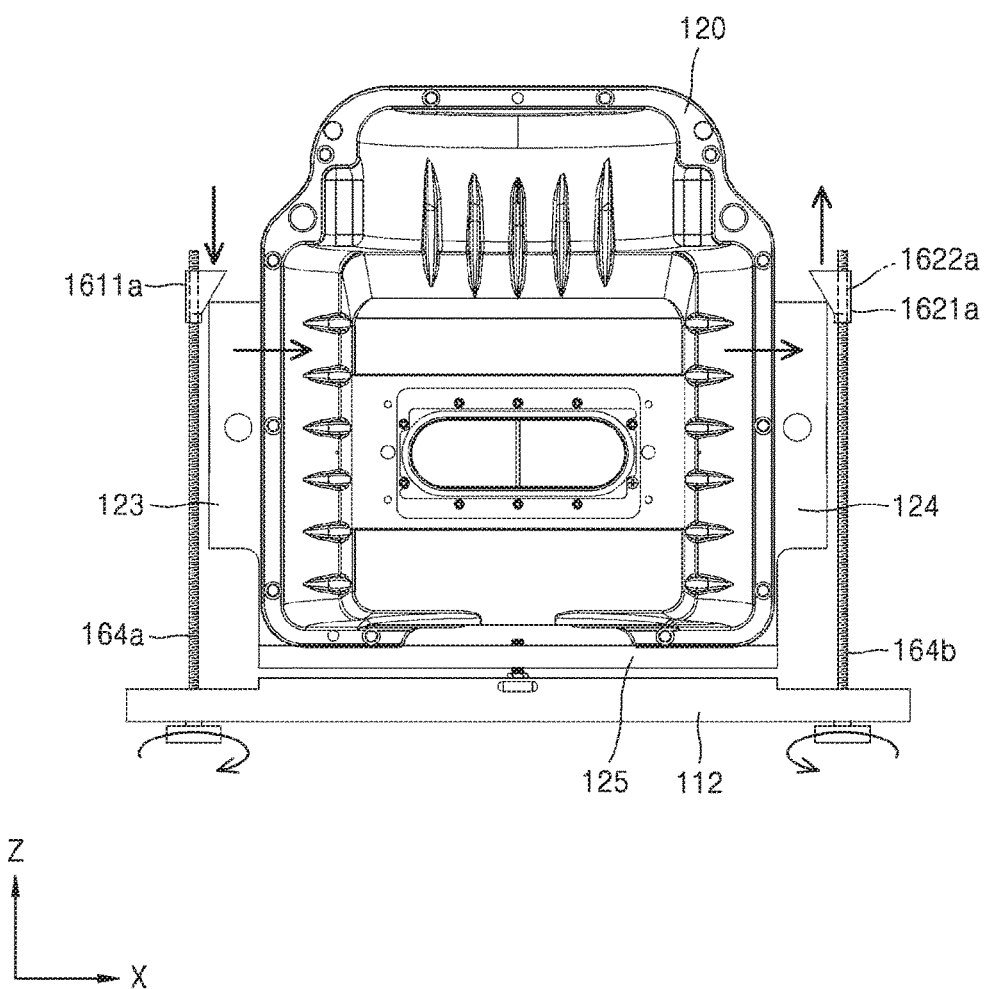
FIG. 7 illustrates a plan view of the radiation emitter, shown in FIGS. 6A and 6B, for explaining movement of a location in an X-axis direction.

FIG. 7 illustrates a plan view of the radiation emitter 120, shown in FIGS. 6A and 6B, for explaining movement of a location in an X-axis direction.

Referring to FIGS. 6B and 7, if a user inserts the precision adjustment tool into the second adjustment hole 1120 and rotates the first lead screw 164a in a clockwise direction, the first lead screws 164a may be moved in a direction in which the subject 10 enters the radiation imaging apparatus 100 along the Z-axis direction. As an example, the second adjustment hole 1120 may be disposed at a front surface of the radiation emitter 120 and, accordingly, a user may easily insert the precision adjustment tool into the second adjustment hole 1120 along a direction in which the second adjustment hole 1120 disposed at the front surface of the radiation emitter 120 extends.

As an example, as described above, as the first lead screw 164*a* rotates in a clockwise direction, a screw of the first lead screw 164*a* may rotate to be engaged with a thread formed on an inner wall of the first insertion hole 1612*a*. Accordingly, the first lead screw 164*a* may move the first pressing unit 161 in a direction opposite to a direction in which the subject 10 enters the radiation imaging apparatus 100 along the Z-axis. The first bearing 166 may support the first lead screw 164*a* so that the first lead screw 164*a* may rotate around the first fixed unit 111.

If a user inserts the precision adjustment tool into the second adjustment hole 1120 and rotates the first lead screw 164*a* and, at the same time, inserts the precision adjustment tool into the second adjustment hole 1120 and rotates the first lead screw 164*b* in a counterclockwise direction, the first lead screw 164*b* may be moved in a direction opposite to a direction in which the first lead screw 164*a* moves. As an example, if the first lead screw 164*b* rotates in a counterclockwise direction, a screw of the first lead screw 164*b* may rotate to be engaged with a thread formed on an inner wall of the first insertion hole 1622*a*. Accordingly, the first lead screw 164*b* may move the second pressing unit 162 in a direction opposite to a direction in which the first lead screw 164*a* is moved. Then, the first bearing 166 may support the first lead screw 164*b* so that the first lead screw 164*b* may rotate around the first fixed unit 111.

If the first pressing unit 161 and the second pressing unit 162 move along a Z axis in different directions from each other, one of the first protruding unit 123 and the second protruding unit 124 which are disposed to respectively contact and support the first inclined unit 1611*a* and the second inclined unit 1621*a* may receive a force along an X-axis direction from one of the first pressing unit 161 and the second pressing unit 162, and the other of the first protruding unit 123 and the second protruding unit 124 may be disengaged from one of the first pressing unit 161 and the second pressing unit 162. Accordingly, the first protruding unit 123, the second protruding unit 124, and the radiation emitter 120 disposed to be fixed to the first protruding unit 123 and the second protruding unit 124 may move along the X-axis direction.

A description about calculation of an amount in which the radiation emitter 120 is moved according to the second angle β with respect to the first and second inclined units 1611*a* and 1621*a* and a pitch P of threads of the first and second lead screws 164*a*, 164*b*, and 165, movement of the radiation emitter 120 in the Z-axis direction, and calculation of an amount in which the radiation emitter 120 is moved in the Z-axis direction are substantially identical to a description provided with reference to FIGS. 4A, 4B, and 5. Thus, the description thereof is not provided here again.

Figure 8A:
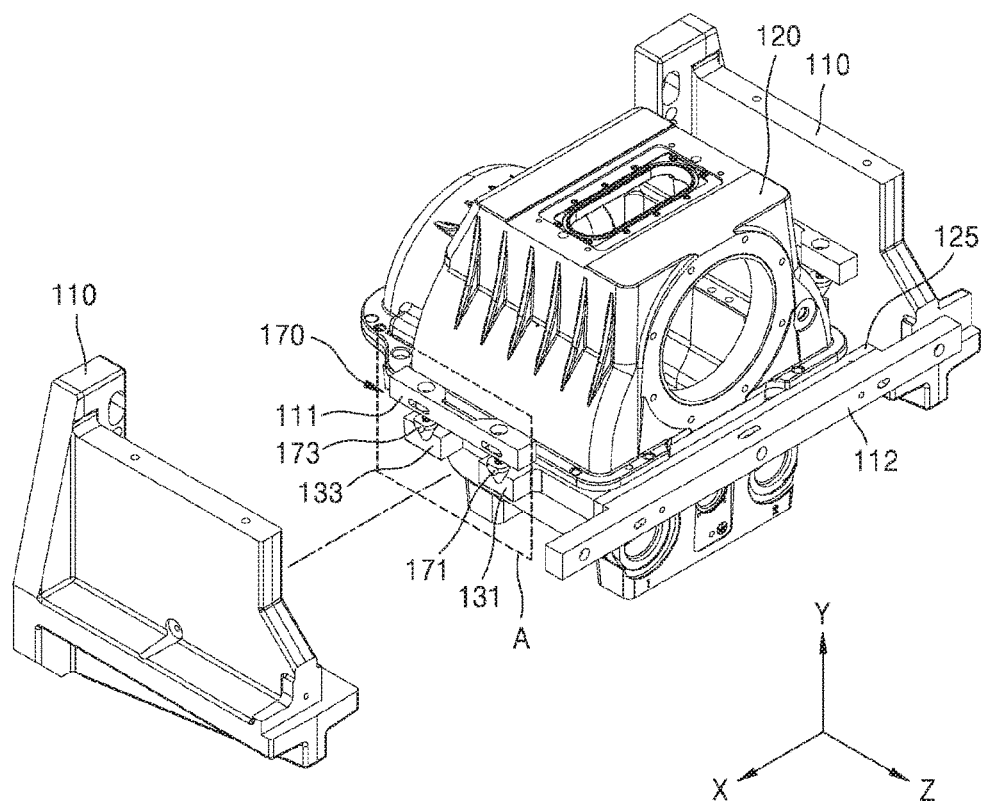
FIG. 8A illustrates a perspective view of the radiation emitter according to another exemplary embodiment.
Figure 8B:
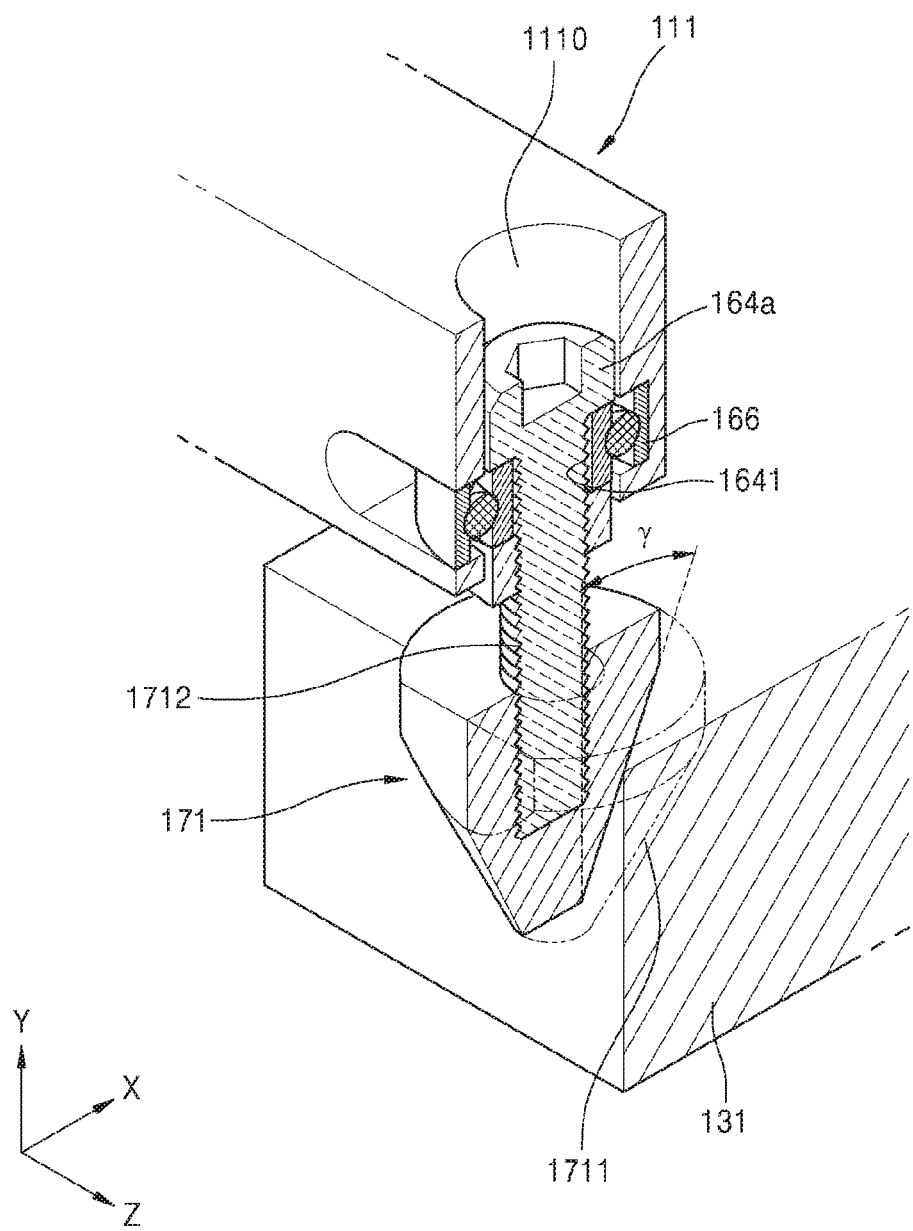
FIG. 8B illustrates a magnified perspective view of an area A shown in FIG. 8A.

FIG. 8A illustrates a perspective view of the radiation emitter 120 according to another exemplary embodiment, and FIG. 8B illustrates a magnified perspective view of an area A shown in FIG. 8A. For convenience of description, a description about elements identical to those shown in FIGS. 3A and 3B is not provided here again.

Referring to FIGS. 8A and 8B, the first protruding unit 131 and the third protruding unit 133 may be disposed at one side of the radiation emitter 120 with a certain space therebetween, and the second protruding unit 132 and the fourth protruding unit 134 may be disposed at another side of the radiation emitter 120 with a certain space therebetween. The alignment adjustment unit 170 may include first through fourth pressing units 171 through 174 that may be disposed to support the first through fourth protruding units 131 through 134, first lead screws 164*a* through 164*d* that may move the first through fourth pressing units 171 through 174, and the first bearing 166 that is disposed at an end of the first lead screws 164*a* through 164*d*.

The first through fourth protruding units 131 through 134 are driving force-delivering members that are disposed to be fixed to both sides of the radiation emitter 120 and may deliver a force, applied from outside, to the radiation emitter 120. As an example, the first through fourth protruding units 131 through 134 may deliver a force, applied from outside, to the radiation emitter 120, and thus, move the radiation emitter 120 in the X-axis direction or rotate the radiation emitter 120 along the Y axis. The first through fourth protruding units 131 through 134 may contact and be supported by the first through fourth pressing units 171 through 174, which will be described later. The first protruding unit 131 and the second protruding unit 132, and the third protruding unit 133 and the fourth protruding unit 134 may be respectively disposed to face each other at both sides of the radiation emitter 120.

For example, the first through fourth pressing units 171 through 174 may be formed in the shape of a cone, and may include first through fourth side surfaces 1711 through 1741 that may respectively contact the first through fourth protruding units 131 through 134 at one point so as to apply a force to the first through fourth protruding units 131 through 134 in the X-axis direction, and first insertion holes 1712 into which the first lead screws 164*a* through 164*d* that may move the first through fourth pressing units 171 through 174 in the Y-axis direction may be inserted.

The first side surface 1711 and the third side surface 1731 may be formed so that generating lines of the first side surface 1711 and the third side surface 1731 are inclined at a third angle γ with respect to a Y-axis, in a clockwise direction. The second side surface 1721 and the fourth side surface 1741 may be formed so that generating lines of the second side surface 1721 and the fourth side surface 1741 are inclined at the third angle γ with respect to the Y-axis, in a counterclockwise direction. Accordingly, if the first through fourth pressing units 171 through 174 move in the Y-axis direction, the first through fourth protruding units 131 through 134 that contact the first through fourth side surfaces 1711 through 1741 may be moved in the X-axis direction. Threads, with which screws formed on the first lead screws 164*a* through 164*d* are engaged and rotate, may be formed on an inner wall of the first insertion holes 1712.

The first lead screws 164*a* through 164*d* may be inserted into the first insertion holes 1712, and move the first through fourth pressing units 171 through 174 along a Y-axis direction. The first fixed unit 111 may include the first adjustment hole 1110 into which the first lead screws 164*a* through 164*d* may be inserted. A user may adjust a location of the radiation emitter unit 120 by inserting an adjustment tool into the first adjustment hole 1110 and rotating the first lead screws 164*a* through 164*d*. The first bearing 166 may be disposed at an end of the first lead screws 164*a* through 164*d* in a direction of a length of the first lead screws 164*a* through 164*d* and supported by the first fixed unit 111 fixed to the housing 105, and thus, support the first lead screws 164*a* through 164*d* so that the first lead screws 164*a* through 164*d* may rotate.

Figure 9A:
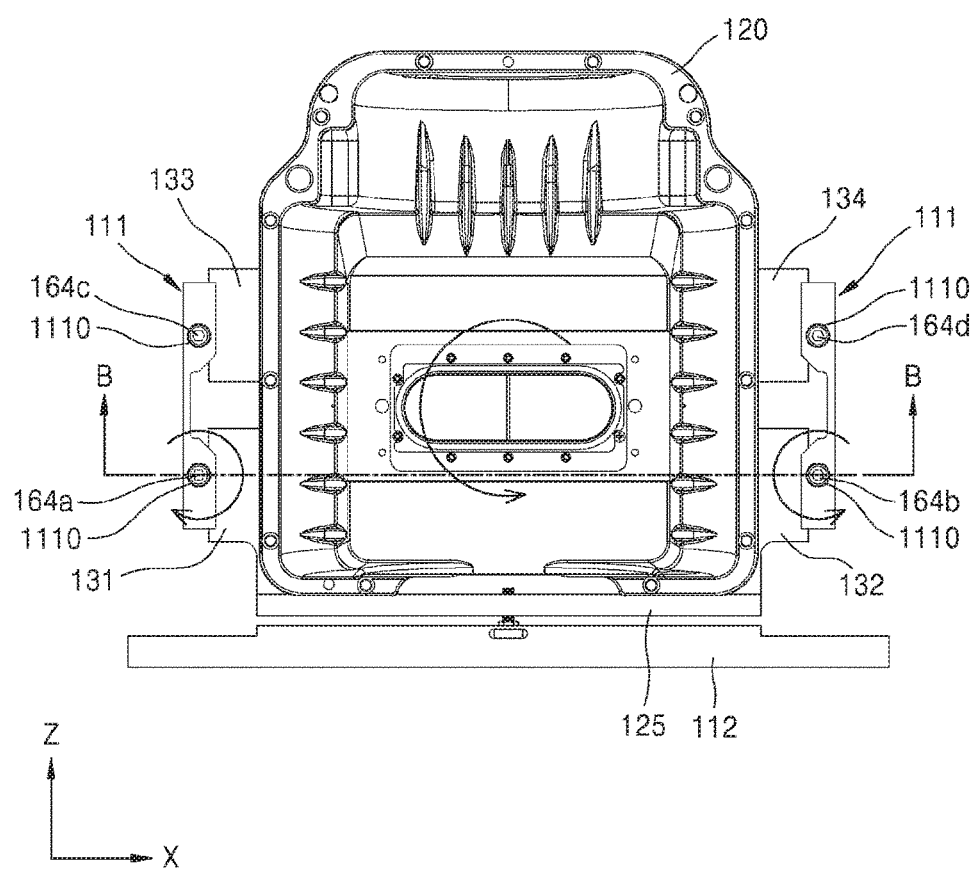
FIG. 9A illustrates a plan view of the radiation emitter, shown in FIG. 8A, for explaining tile adjustment with reference to a Y-axis.
Figure 9B:
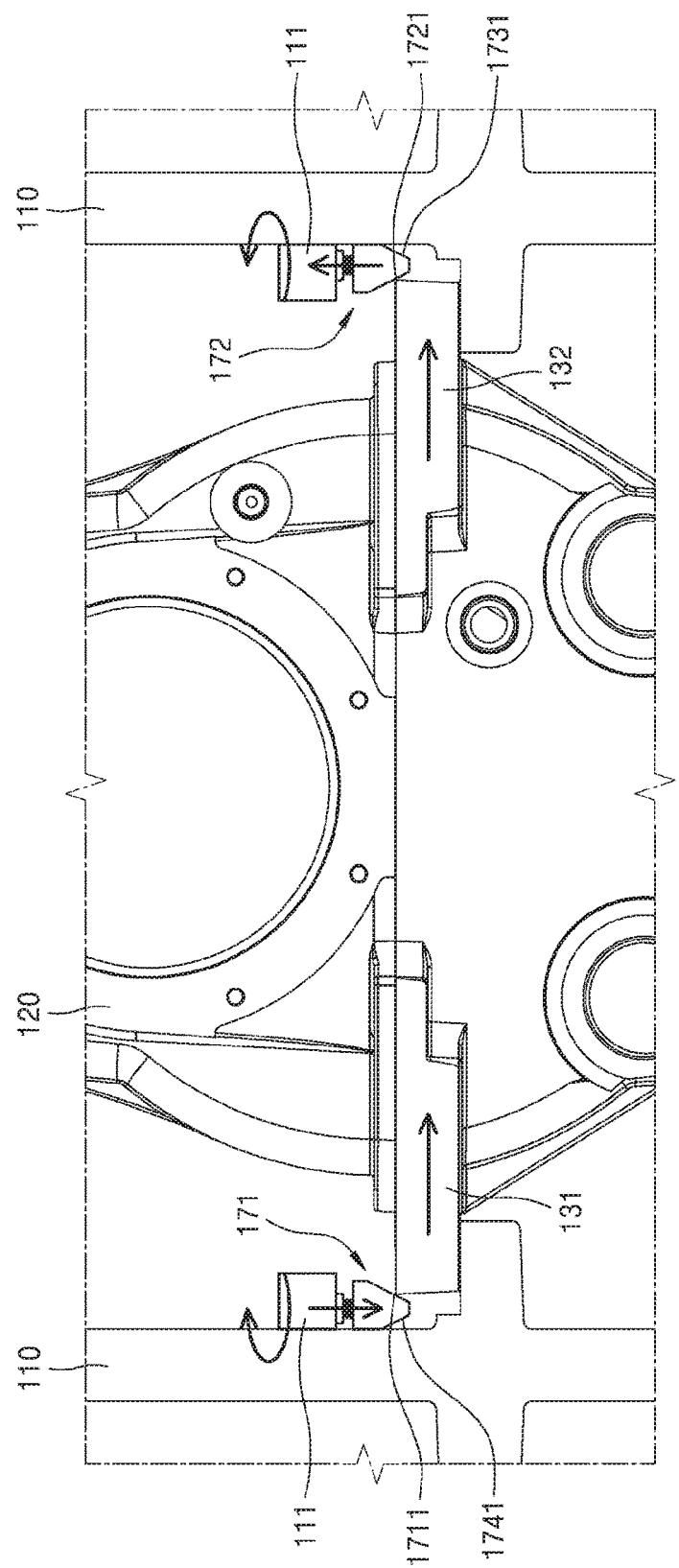
FIG. 9B illustrates a sectional view of the radiation emitter, shown in FIG. 8A, which is taken along a line B-B.

FIG. 9A illustrates a plan view of the radiation emitter 120, shown in FIG. 8A, for explaining tile adjustment along a Y-axis, and FIG. 9B illustrates a sectional view of the radiation emitter 120, shown in FIG. 9A, which is taken along line B-B.

Referring to FIGS. 8B, 9A, and 9B, if a user inserts the precision adjustment tool into the first adjustment hole 1110 and rotates the first lead screw 164a in a clockwise direction, the first lead screw 164a may be moved in a direction in which radiation is emitted along the Y-axis direction. As an example, the first adjustment hole 1110 may be disposed at a side of the radiation emitter 120 and, accordingly, the user may easily insert the precision adjustment tool into the first adjustment hole 1110 along a direction in which the first adjustment hole 1110 disposed at the side of the radiation emitter 120 extends.

As an example, as shown in FIG. 9B, if the first lead screw 164a rotates in a clockwise direction, a screw of the first lead screw 164a may rotate to be engaged with a screw thread formed on an inner wall of a first insertion hole 1712. Accordingly, the first lead screw 164a may move the first pressing unit 171 in a direction in which radiation is emitted. Then, the user may move the first lead screw 164b in a direction opposite to a direction in which the first lead screw 164a moves, by inserting the precision adjustment tool into the first adjustment hole 1110 and rotating the first lead screw 164b in a counterclockwise direction.

Additionally, the user may rotate and move the first lead screw 164a and the second lead screw 165 in the Y-axis direction and, at the same time, does not rotate the first lead screws 164c and 164d. Accordingly, the third pressing unit 173 and the third pressing unit 174 may support the third protruding unit 133 and the fourth protruding unit 134 without moving in the Y-axis direction. Additionally, the first bearing 166 may support the first lead screws 164a and 164b so that the first lead screws 164a and 164b may rotate around the first fixed unit 111.

As the first pressing unit 171 and the second pressing unit 172 move along the Y axis in different directions from each other, the first protruding unit 131 may receive a force from the first pressing unit 171 along the X axis, and the second protruding unit 132 may be disengaged from the second pressing unit 172, and thus, does not receive any force. On the contrary, since the third pressing unit 173 and the fourth pressing unit 174 do not move in the Y-axis direction, the third protruding unit 133 and the fourth protruding unit 134 may be supported by the third pressing unit 173 and the fourth pressing unit 174. Accordingly, a force applied to the first pressing unit 171 by the first pressing unit 171 may apply a rotational force to the radiation emitter 120 with reference to the Y-axis. For example, if the first pressing unit 171 applies a force to the first protruding unit 131 in the X-axis direction, the radiation emitter 120 may be rotated in a clockwise direction. Accordingly, a user may adjust a tilt of the radiation emitter 120, the subject 10, and the radiation detector 130, by rotating the radiation emitter 120 by using the first lead screws 164a and 164b.

Figure 10:
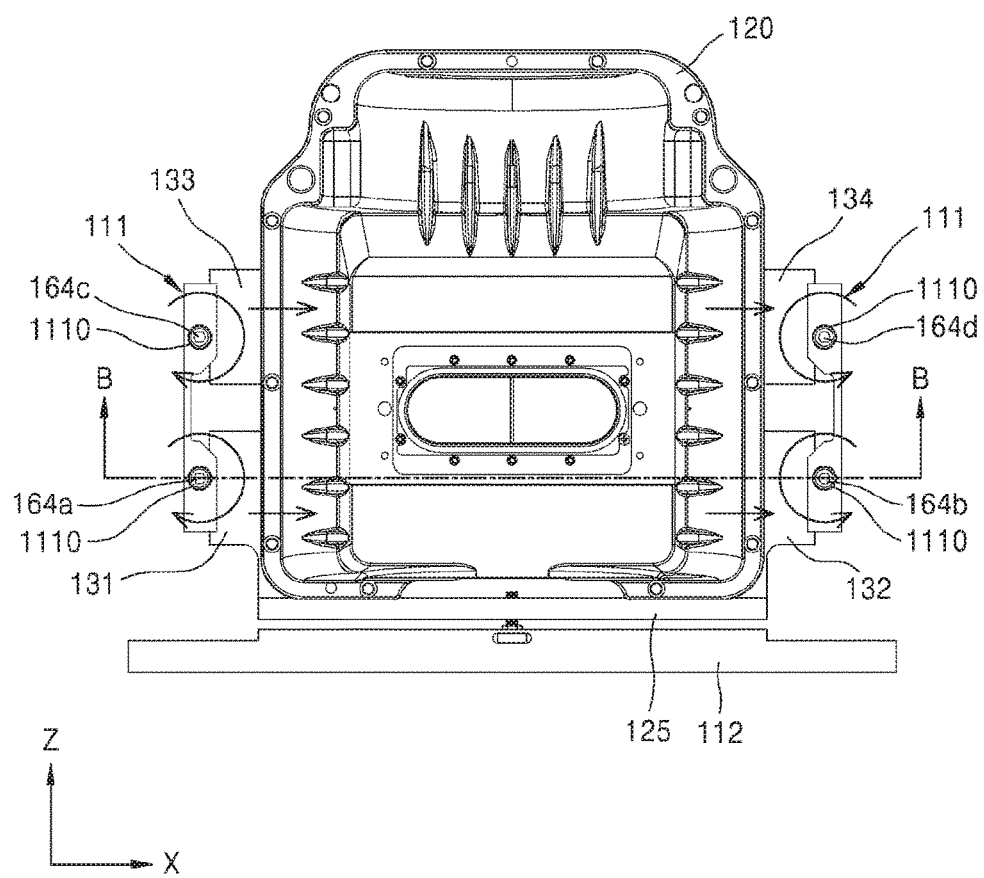
FIG. 10 illustrates a plan view of the radiation emitter, shown in FIG. 8A, for explaining alignment adjustment in an X-axis direction.

FIG. 10 illustrates a plan view of the radiation emitter 120, shown in FIG. 8A, for explaining alignment adjustment in an X-axis direction.

Referring to FIGS. 8B and 10, if a user inserts the precision adjustment tool into the first adjustment hole 1110 and rotates the first lead screws 164a and 164c in a clockwise direction, the first lead screws 164a and 164c may be moved in a direction in which radiation is emitted along a Y-axis direction. Then, if the user inserts the precision adjustment tool into the first adjustment hole 1110 and rotates the first lead screws 164b and 164c in a counterclockwise direction, the first lead screws 164b and 164d may be moved in a direction opposite to a direction in which the first lead screw 164a moves. Accordingly, the first pressing unit 171 and the third pressing unit 173 may be moved in a direction in which radiation is emitted along the Y-axis, and the second pressing unit 172 and the fourth pressing unit 174 may be moved in a direction opposite to a direction in which the first pressing unit 171 and the third pressing unit 173 move.

As the first pressing unit 171 and the third pressing unit 173, and the second pressing unit 172 and the fourth pressing unit 174 are moved along the Y-axis in directions different from each other, the first protruding unit 131 and the third protruding unit 133 may receive a force along the X-axis direction from the first pressing unit 171 and the third pressing unit 173, and the second protruding unit 132 and the fourth protruding unit 134 may be disengaged from the second pressing unit 172 and the fourth pressing unit 174, and thus, may not receive any force. Thus, a force applied to radiation emitter 120 by the first pressing unit 171 and the third protruding unit 173 may move the radiation emitter 120 in the X-axis direction. Accordingly, the user may adjust alignment of the radiation emitter 120, the subject 10, and the radiation detector 130 in the X-axis direction, by rotating the radiation emitter 120 by using the first lead screws 164a through 164d.

A description about movement of the radiation emitter 120 in the Z-axis direction is substantially identical to a description provided with reference to FIGS. 4 and 5, and thus, is not provided here again.

Figure 11:
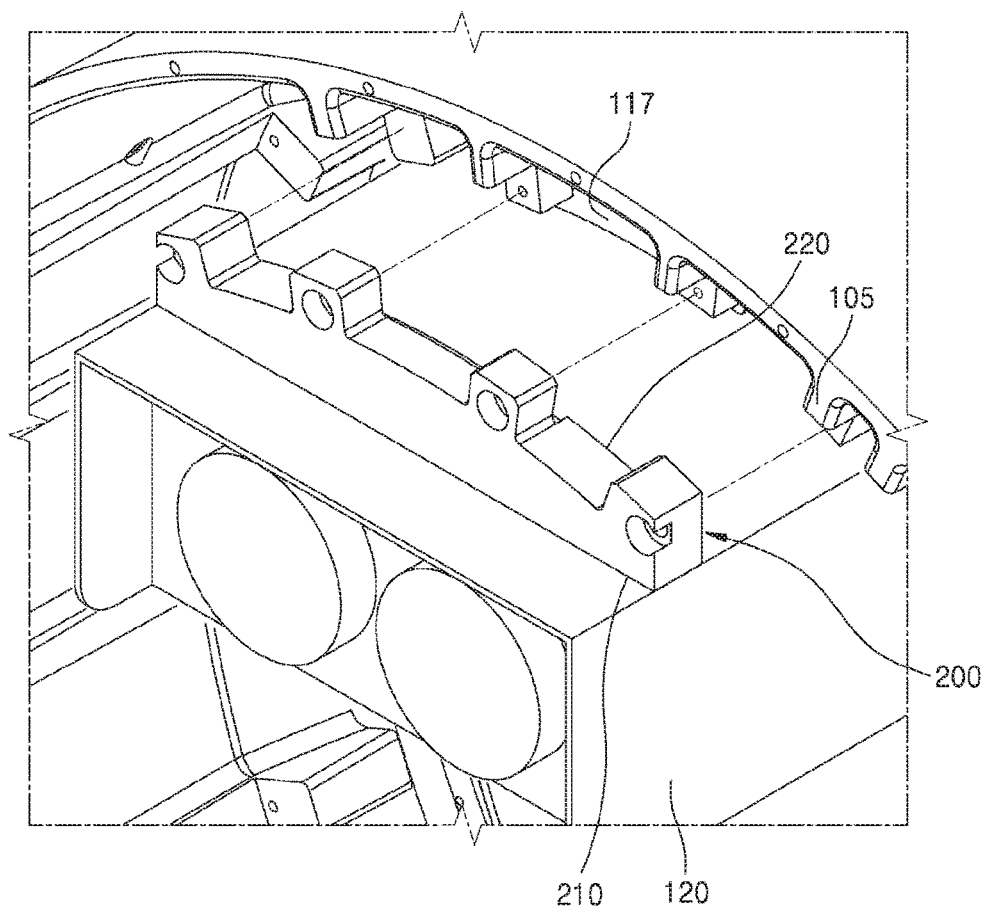
FIG. 11 illustrates a magnified perspective view of a part of the radiation imaging apparatus according to another exemplary embodiment.
Figure 12A:
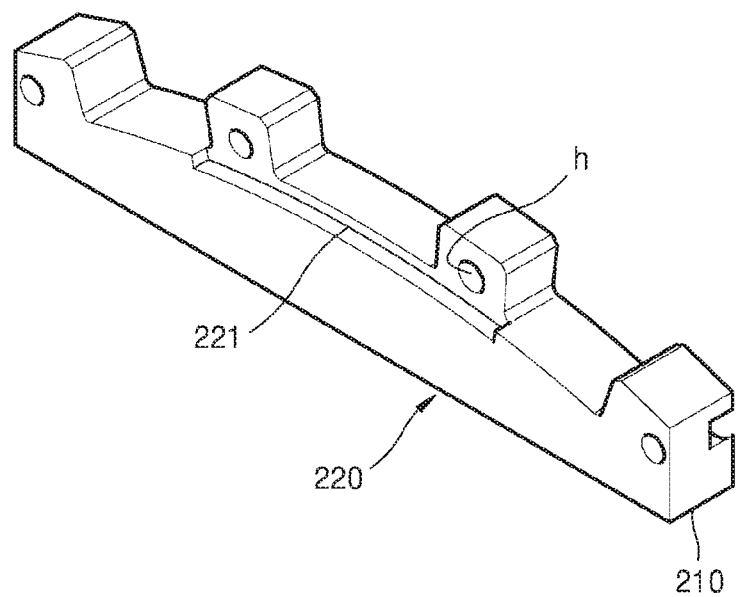
FIG. 12A illustrates a perspective view of a bracket shown in FIG. 11.
Figure 12B:
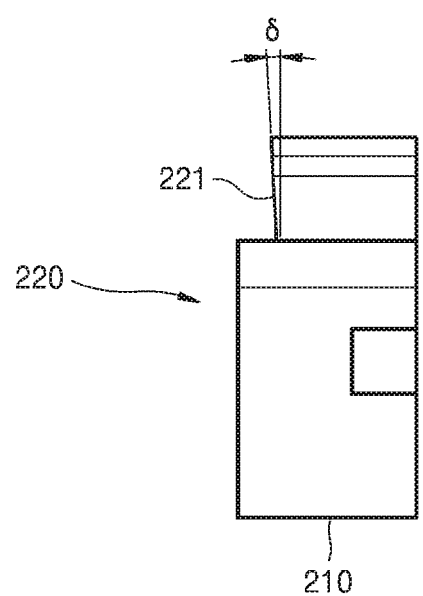
FIG. 12B illustrates a side view of the bracket shown in FIGS. 11.
Figure 13:
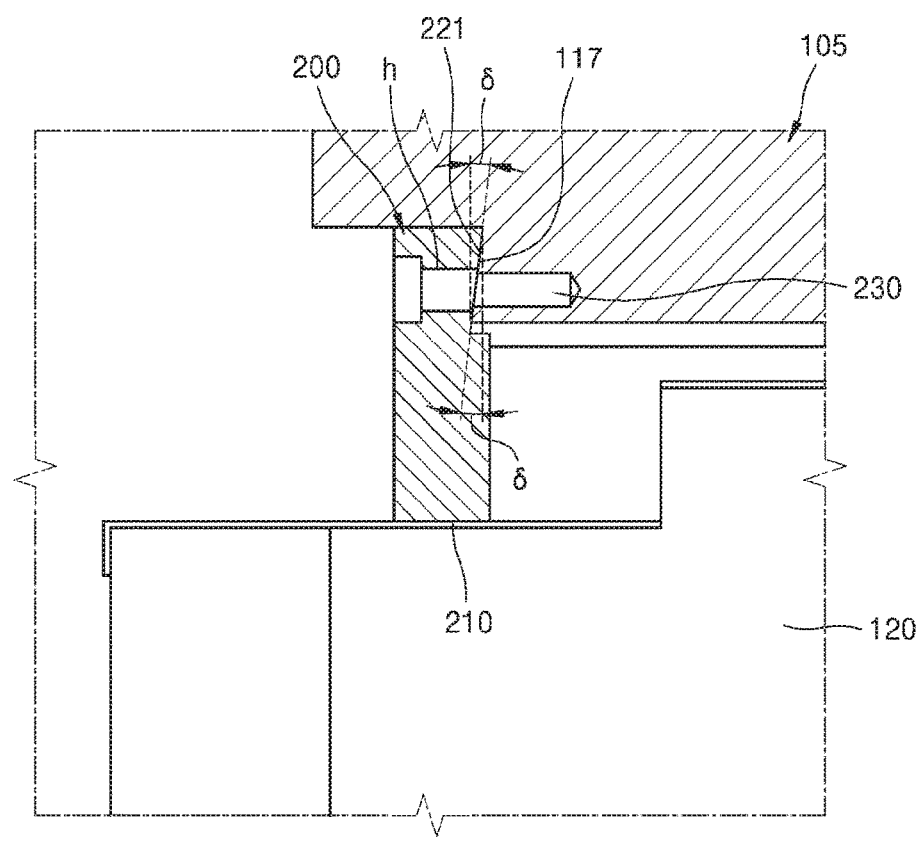
FIG. 13 illustrates a cross-sectional view of the radiation imaging apparatus shown in FIG. 11.

FIG. 11 illustrates a magnified perspective view of a part of the radiation imaging apparatus 100 according to another exemplary embodiment. FIG. 12A illustrates a perspective view of a bracket 200 shown in FIG. 11, and FIG. 12B illustrates a side view of the bracket shown in FIG. 11. FIG. 13 illustrates a cross-sectional view of the radiation imaging apparatus 100 shown in FIG. 11.

As shown in FIGS. 1 and 2, the radiation imaging apparatus 100 may include the housing 105 and the radiation emitter 120. The radiation emitter 120 may be aligned in the housing 105 so that the radiation emitter 120 and the housing 105 may support each other. According to an exemplary embodiment, the radiation imaging apparatus 100 may include the bracket 200 for engaging the housing 120 with the radiation emitter 120.

Referring to FIGS. 11, 12A, and 12B, the bracket 200 is a member for fixedly installing the radiation emitter 120 in the housing 105. For example, the radiation emitter 120 may be installed in the housing 106 by the bracket 200 so that the radiation emitter 120 is fixed in the housing 105. The bracket 200 may include a radiation emitter-supporting unit 210 for supporting the radiation emitter 120, and a housing-support plate 220 connected to a surface 117 of the housing 105. The radiation emitter-supporting unit 210 may be formed at an end of the housing support plate 220. One or more through holes h, through which a bolt unit 230 that is to be described later may pass, may be formed on the housing support plate 220. As an example, the through hole h may be disposed at a front surface of the radiation emitter 120 and, accordingly, the user may easily insert the precision adjustment tool into the through hole h along a direction in which the through hole h disposed at the front surface of the radiation emitter 120 extends. A surface 221 of the housing support plate 220, which is disposed to face a surface 117 of the housing 105, may be formed to be inclined in a clockwise direction in correspondence with a fourth angle δ with respect to an optical direction of radiation, that is, the Y-axis direction.

Referring to FIGS. 11 and 13, as an example, one or more bolt units 230 are disposed to respectively correspond to one or more through holes h formed on the housing support plate 22, and connect the housing to the bracket 200. The surface 117 of the housing 105 may be formed to be inclined in a counterclockwise direction in correspondence with the fourth angle δ with respect to an optical direction of radiation, that is, the Y-axis direction, so that the surface 117 of the housing 105 may be engaged with the surface 221 of the housing support plate 220. As an example, the fourth angle δ may be equal to or less than 5.6°.

If the radiation emission unit 120 is fixedly connected to the housing 105, the surface 117 of the housing 105 and the surface 221 of the housing support plate 220 may be disposed to face and support each other. As described above, since the surface 117 of the housing 105 and the surface 221 of the housing support plate 220 are formed to be inclined in correspondence with the fourth angle δ respectively in a clockwise direction and in a counterclockwise direction, an engaging force between the housing 105 and the bracket 200 is increased, and thus, movement of the radiation emitter 120 in the Y-axis direction may be prevented. Accordingly, a relative position of the radiation emitter 120 with respect to the housing 105 may be fixed, and the subject 10 and the radiation emitter 120 which may be disposed in the housing 105 may not be misaligned.

The use of any and all examples, or exemplary language (e.g., "such as") provided herein, is intended merely to better illuminate the exemplary embodiments and does not pose a limitation on the scope of the exemplary embodiments unless otherwise claimed. Numerous modifications and adaptations will be readily apparent to those skilled in this art without departing from the spirit and scope of the exemplary embodiments.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A radiation imaging apparatus comprising:
   a housing configured to be hollow and extend along a first axial direction;
   a radiation emitter configured to be disposed in the housing and emit radiation along an optical axial direction perpendicular to the first axial direction;
   protruding units configured to extend along a second axial direction perpendicular to the first axial direction and the optical axial direction, and disposed to be fixed to both sides of the radiation emitter; and
   pressing units comprising an inclined unit disposed to contact at least one of the protruding units, so that the inclined unit and the at least one of the protruding units support each other.

2. The radiation imaging apparatus of claim 1, wherein the protruding units include a first protruding unit and a second protruding unit disposed to face each other at the both sides of the radiation emitter,
   the pressing units include a first pressing unit including a first inclined unit and a second pressing unit including a second inclined unit, which are disposed so that the first inclined unit and the first protruding unit support each other and the second inclined unit and the second protruding unit support each other,
   the first and second inclined units form respective first angles with respect to the optical axial direction, and
   the radiation emitter moves along the second axial direction as the first pressing unit and the second pressing unit, together with the first inclined unit and the second inclined unit, respectively, move in directions different from each other along the optical axial direction.

3. The radiation imaging apparatus of claim 2, further comprising first lead screws that are respectively disposed to be inserted into the first and second pressing units, and move the first and second pressing units along the optical axial direction as the first lead screws rotate.

4. The radiation imaging apparatus of claim 3, wherein a degree to which the radiation emitter moves according to a rotation of the first lead screws is determined by a number of times the first lead screws rotate and the first angles formed by the first and second inclined units, respectively.

5. The radiation imaging apparatus of claim 1, further comprising:
   a support unit disposed to be fixed to the radiation emitter; and
   a second lead screw disposed to be inserted into the support unit,
   wherein the support unit is moved along the first axial direction as the second lead screw rotate.

6. The radiation imaging apparatus of claim 5, wherein a degree to which the radiation emitter moves along the first axial direction is determined according to a number of times the second lead screw rotates.

7. The radiation imaging apparatus of claim 1, wherein the protruding units include a first protruding unit and a second protruding unit disposed to face each other at the both sides of the radiation emitter,
   the pressing units include a first pressing unit including a first inclined unit and a second pressing unit including a second inclined unit, which are disposed so that the first inclined unit and the first protruding unit support each other and the second inclined unit and the second protruding unit support each other,
   the first and second inclined unit form respective second angles with respect to the first axial direction, and
   the radiation emitter moves along the second axial direction as the first pressing unit and the second pressing unit, together with the first inclined unit and the second inclined unit, respectively, move in directions different from each other along the first axial direction.

8. The radiation imaging apparatus of claim 7, further comprising:
   first lead screws disposed to be inserted into the first and second pressing units,
   wherein the first and second pressing units are moved along the first axial direction as the first lead screws rotate.

9. The radiation imaging apparatus of claim 8, wherein a degree to which the radiation emitter moves according to a rotation of the first lead screws is determined according to a number of times the first lead screws rotate and the second angle formed by the first and second inclined units, respectively.

10. A radiation imaging apparatus comprising:
a housing configured to be hollow and extend along a first axial direction;
a radiation emitter configured to be disposed in the housing and emit radiation along an optical axial direction perpendicular to the first axial direction;
protruding units that are formed to extend along a second axial direction perpendicular to the first axial direction and the optical axial direction, and disposed to be fixed to both sides of the radiation emitter; and
pressing units each comprising a side surface having a shape of a cone, which has a generating line formed to establish an angle with the optical axial direction,
wherein the side surface of a respective pressing unit and a respective protruding unit are in contact with each other and support each other.

11. The radiation imaging apparatus of claim 10, wherein the protruding units include a first protruding unit and a second protruding unit, and a third protruding unit and a fourth protruding unit that are respectively disposed to face each other at both ends of the radiation emitter,
the pressing units include a first pressing unit and a second pressing unit, which are disposed so that the first pressing unit and the first protruding unit support each other and the second pressing unit and the second protruding unit support each other, and a third pressing unit and a fourth pressing unit, which are disposed so that the third pressing unit and the third protruding unit support each other and the fourth pressing unit and the fourth protruding unit support each other, and
the radiation emitter is tilted with respect to the optical axial direction, as the first pressing unit and the second pressing unit move along the optical axial direction in directions different from each other and the third pressing unit and the fourth pressing unit are fixed to the third pressing unit and the fourth protruding unit.

12. The radiation imaging apparatus of claim 11, wherein the radiation emitter moves along the second axial direction as the first pressing unit and the third pressing unit, and the second pressing unit and the fourth pressing unit respectively move in directions opposite to each other along the first axial direction.

13. The radiation imaging apparatus of claim 12, further comprising:
first lead screws disposed to be inserted into the first, second, third, and fourth pressing units,
wherein the first, second, third, and fourth pressing units are moved along the optical axial direction as the first lead screws rotate.

14. The radiation imaging apparatus of claim 13, wherein a degree to which the radiation emitter moves according to a rotation of the first lead screws is determined by a number of times the first lead screws rotate and the angle between the generating line of the side surface and the optical axial direction.

15. The radiation imaging apparatus of claim 10, further comprising:
a support unit disposed to be fixed to the radiation emitter; and
a second lead screw disposed to be inserted into the support unit,
wherein the support unit is moved along the first axial direction as the second lead screws rotates.

16. The radiation imaging apparatus of claim 15, wherein a degree to which the radiation emitter moves along the first axial direction is determined according to a number of times the second lead screw rotates.

17. A radiation imaging apparatus comprising:
a housing configured to be hollow and extend along a first axial direction;
a radiation emitter configured to be disposed in the housing and emit radiation along an optical axial direction perpendicular to the first axial direction; and
a bracket that is disposed between the radiation emitter and the housing and supports the radiation emitter so that the radiation emitter is fixed to the housing, the bracket including a surface disposed to face a surface of the housing extending in the optical axial direction, the surface of the bracket and the surface of the housing being tilted in correspondence with an angle in the optical axial direction.

18. The radiation imaging apparatus of claim 17, further comprising:
bolts that are formed to extend in the first axial direction, and disposed so that an end of each of the bolts is fixed to the surface of the housing; and
through-holes which are disposed at the bracket to respectively correspond to the bolts and through which the bolts are inserted for fixing the bracket to the housing.

19. The radiation imaging apparatus of claim 17, wherein the angle is equal to or less than 5.6°.

* * * * *